Figure 1:
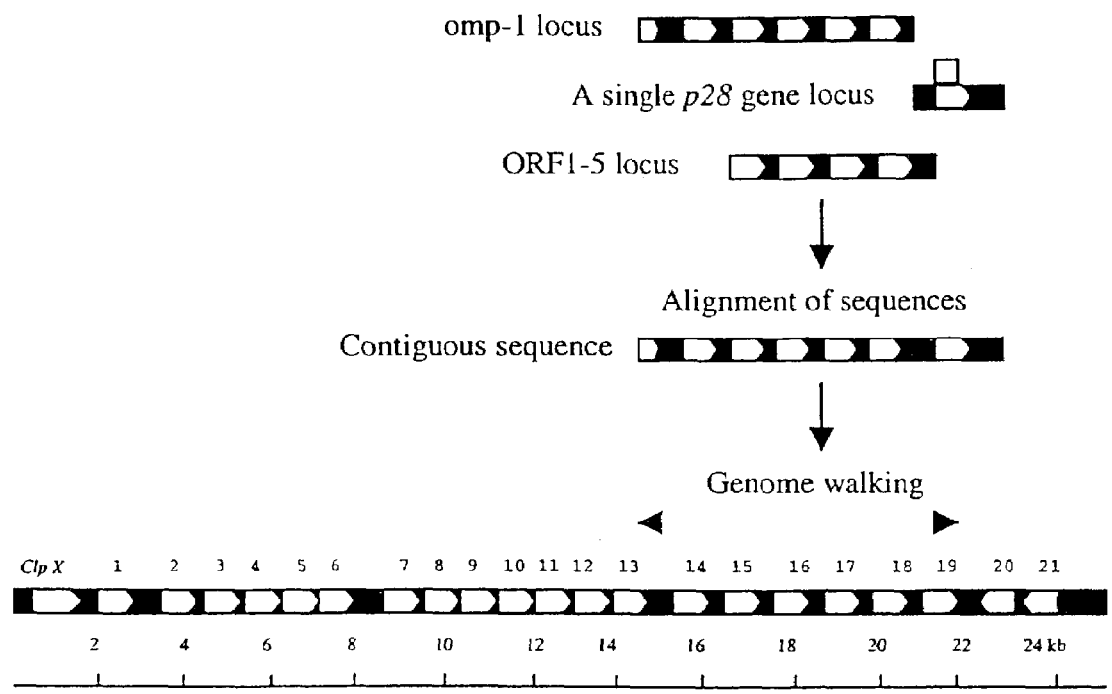

United States Patent
Walker et al.

(10) Patent No.: US 7,332,171 B2
(45) Date of Patent: Feb. 19, 2008

(54) EHRLICHIA CHAFFEENSIS 28 KDA OUTER MEMBRANE PROTEIN MULTIGENE FAMILY

(75) Inventors: David H. Walker, Galveston, TX (US); Xue-Jie Yu, Galveston, TX (US)

(73) Assignee: Research Development Foundation, Carson City, NV (US)

( * ) Notice: Subject to any disclaimer, the term of this patent is extended or adjusted under 35 U.S.C. 154(b) by 485 days.

(21) Appl. No.: 10/369,293

(22) Filed: Feb. 18, 2003

(65) Prior Publication Data

US 2003/0147913 A1 Aug. 7, 2003

Related U.S. Application Data

(62) Division of application No. 09/846,808, filed on May 1, 2001, now abandoned.

(60) Provisional application No. 60/201,035, filed on May 1, 2000.

(51) Int. Cl.
- *A61K 39/02* (2006.01)
- *C12P 21/02* (2006.01)
- *C07H 21/04* (2006.01)
- *C12N 15/09* (2006.01)

(52) U.S. Cl. ............... 424/234.1; 424/190.1; 435/69.3; 435/69.7; 435/326; 435/340; 435/331; 530/350; 530/387; 530/388.1; 536/23.5

(58) Field of Classification Search ............... 536/23.4, 536/23.7, 23.5; 435/69.7, 326, 340, 331; 435/69.3; 530/387, 388.1, 350; 424/234.1, 424/190

See application file for complete search history.

(56)

U.S. PATENT DOCUMENTS

| | | |
|---|---|---|
| 6,392,023 B1 | 5/2002 | Walker et al. .............. 536/23.1 |
| 6,403,780 B1 | 6/2002 | Walker et al. .............. 536/23.1 |
| 6,544,517 B1 * | 4/2003 | Rikihisa et al. ........... 424/184.1 |

OTHER PUBLICATIONS

Verma et al. (1997) Nature, vol. 389, p. 239-42).*
Marshall. (1995) Science, vol. 269, p. 1050-1055.*
Orkin et al. (1995) NIH report.*
Burgess et al., The Journal of Cell Biology, 111:2129-2138, 1990.*
Jobling et al. (Mol. Microbiol. 1991, 5(7): 1755-67.*
Sequence alignment with U72291.*
Sequence alignment with 6544517.*
U.S. Appl. No. 60/059,353, filed Sep. 19, 1997, Rikihisa et al.
Anderson et al., "*Ehrlichia chaffeensis*, a new species associated with human ehrlichiosis," *J Clin Microbiol*, 29(12):2838-2842, 1991.
Anderson et al., "*Ehrlichia ewingii* sp. Nov., the etiologic agent of canine granulocytic ehrlichiosis" *Int J Syst Bacteriol*, 42(2):299-302, 1992.
Brouqui et al., "Antigenic characterization of ehrlichiae: protein immunoblotting of *Ehrlichia canis, Ehrlichia sennetsu*, and *Ehrlichia risticii*," *J Clin Microbiol*, 30(5):1062-1066, 1992.
Burgess et al., "Possible dissociation of the heparin-binding and mitogenic activities of heparin-binding (acidic fibroblast) growth factor-1 from its receptor-binding activities by site-directed mutagenesis of a single lysine residue," *J. Cell. Biol.*, 111:2129-2138, 1990.
Chen et al., "Identification of the antigenic constituents of *Ehrlichia chaffeensis*," *Am J Trop Med Hyg*, 50(1):52-58, 1994.
Chen et al., "Western immunoblotting analysis of the antibody responses of patients with human monocytotropic ehrlichiosis to different strains of *Ehrlichia chaffeensis* and *Ehrlichia canis*," *Clin Diag Lab Immunol*, 4(6):731-735, 1997.
Dawson et al., "Serologic diagnosis of human ehrlichiosis using two *Ehrlichia canis* isolates," *J Infect Dis*, 163:564-567, 1991.
GenBank Accession No. AAY069965.
GenBank Accession No. AF078553.
GenBank Accession No. AF082744.
GenBank Accession No. AF230642.
GenBank Accession No. U72291.
GenBank Accession No. AAK28699.
GenBank Accession No. AAC68666.
GenBank Accession No. AF078555.
Groves et al., "Transmission of *Ehrlichia canis* to dogs by ticks (*Rhipicephalus sanguineus*)," *Am J Vet Res*, 36:937-940, 1975.
Harrus et al., "Amplification of ehrlichial DNA from dogs 34 months after infection with *Ehrlichia canis*," *J Clin Microbiol*, 36(1):73-76, 1998.
Jobling et al., "Analysis of structure and function of the B subunit of cholera toxin by the use of site-directed mutagenesis," *Mol. Microbiol.*, 5:1755-1767, 1991.

Jongejan et al., "The immunodominant 32-kilodalton protein of Cowdria ruminantium is conserved within the genus *Ehrlichia*," *Rev Elev Med Vet Pays Trop*, 46(1-2):145-152, 1993.
McBride et al., "A conserved, transcriptionally active p28 multigene locus of *Ehrlichia canis*," Gene, 254:245-252, 2000.
McBride et al., "Molecular cloning of the gene for a conserved major immunoreactive 28-kilodalton protein of *Ehrlichia canis*: a potential serodiagnostic antigen," *Clinical and Diagnostic Laboratory Immunobiology*, 6(3):392-399, 1999.
McClure, "Mechanism and control of transcription initiation in prokaryotes," *Ann Rev Biochem*, 54:171-204, 1985.
Ohashi et al., "Cloning and characterization of multigenes encoding the immunodominant 30-kilodalton major outer membrane proteins of *Ehrlichia canis* and application of the recombinant protein for serodiagnosis," *Journal of Clinical Microbiology*, 36(9):2671-2680, 1998.
Ohashi et al., "Immunodominant major outer membrane proteins of *Ehrlichia chaffeensis* are encoded by a polymorphic multigene family," *Infect Immun*, 66(1):132-139, 1998.
Pharmacia Biotech, *BioDirectory*, Chapter 9, 217-236, 1996.
Reddy et al., "Molecular characterization of a 28 kDa surface antigen gene family of the tribe *Ehrlichiae*," *Biochem Biophys Res Comm*, 247(3):636-643, 1998.
Rikihisa et al., "Western immunoblot analysis of *Ehrlichia chaffeensis, E. canis*, or *E. ewingii* infections in dogs and humans," *J Clin Microbiol*, 32(9):2107-2112, 1994.
Shankarpappa, "Antigenic and genomic relatedness among *Ehrlichia risticii, Ehrlichia sennetsu*, and *Ehrlichia canis*," *Int J Syst Bacteriol*, 42(1):127-132, 1992.
Storey et al., "Molecular cloning and sequencing of three granulocytic *Ehrlichia* genes encoding high-molecular-weight immunoreactive proteins," *Infection and Immunity*, 66(4):1356-1363, 1998.
Yu et al., "Characterization of the complete transcriptionally active *Ehrlichia chaffeensis* 28 kDa outer membrane protein multigene family," *Gene*, 248:59-68, 2000.
Yu et al., "Detection of *Ehrlichia chaffeensis* in human tissue by using a species-specific monoclonal antibody," *J. Clin Microbiol.* 31:3284-3288, 1993.
Li, et al. "Antibodies highly effective in SCID mice during infection by the intracellular bacterium *Ehrlichia chaffeensis* are of picomolar affinity and exhibit preferential epitope and isotype utilization" *Journal of Immunology* 2002, 169:1419-1425.
Singu, et al. "*Ehrlichia chaffeensis* expresses macrophase- and tick cell-specific 28-kilodalton outer membrane proteins" *Infection and Immunity* 2005, vol. 73, No. 1, pp. 79-87.
U.S. Appl. No. 60/100,843, Rikihisa et al.
Singu, V., et al., "*Ehrlichia chaffeensis* Expresses Macrophase- and Tick Cell-Specific 28-Kilodalton Outer Membrane Proteins," Infection and Immunity, (Jan. 2005), pp. 79-87.

* cited by examiner

```
1   MSK-RSNRKFVL----WVMLILFTPHISLASVLNDHN--------SMYVGIQYKPARQHLSKLLIKESAA----N-----  58
2   ....-........-YAKVFILIC...LV.SL.F.I.N....----FLKDNIGHF.I.G...GVPRFNRF.VTNNNIRELMSSDEEC  69
3   ----Q.LYISFIILSG.L--L.KYVFC-----MHQNNNIDGS..T.K.QLTTP.FKNFY..TDF----DTQEP-  60
4   YMYNKKHYCYIVTYVITLFF.LL.IE..SALI--G.VEKDLKVS.T..SS....SIF.FRNFS.Q..HP-----K--  69
5   .TKKFN..NV--ILTF.LFLF.LK.FTTYA--N..NTITQKVGL.ISG....SIP.FKNFSVE.ND-----K--  62
6   .--S-KK..ITIGTVLAS.LS.LSIE.FSAIN--...HTGNNTSGI.ITG...R.GVS.F.NFSV..TNV-----D--  64
7   .--SAKK.LFIIGSVL.C.VSYL.TK..SNLN--NI-NNNTKCTGL..SG....TVS.F.NFSL..TYT-----D--  65
8   .--S-KKN.ITIGATLIHML--L.N..FPETI--N..NTD-KLSGL.ISG....GIS.F..FSV..IYN-----D--  61
9   .--NNRKS.FIIGASLLASL...SEA.STGNV--S..HTYFK-PRL.ISG...R.GVS.F..FSV..TNY-..----  64
10  .--NKKN..I-IATAL.-YL.SL.SV.FSE.T--NS-SIKKH-SGL.ISG....SVSVF.SFS...TNT----I--  62
11  .--NHKSMLFTIGTALI-SL.SL.NV.FSGII--N.-NAN-N-LGI.ISG....SVSVF.NFSV..TNF----T--  62
12  .--KKKNQ.ITISTIL.-CL.SLSNA...SNTT--NS-STKKQ-FGL..SG....SVSIF.NFSV..TNF----P--  63
13  .--NKKN..FTISTAM.-CL.LL.G..FSETI--N.-SAKKQ-PGL.ISG....SVSVF.NFSV..TNV----P--  63
14  .--NYK.IF-VSSALIS.MSIL.YQ.F.DPVTSNDTGINDSREGF.ISVK.N.SIS.FR.FSAE.API----.GNTSI  71
15  .---NCK..F-ITTALALPMS.L.G.L.SEPVQ.DSVS----GNF.ISGK.M.SAS.FGVFSA.....----EKNP  61
16  .--NCE..F-ITTALTL.MS.L.G...SDPVQ.D.IS-----GNF.ISGK.M.SAS.FGVFSA.....----ERNT  61
17  .--NCK..F-ITTAL.S.MS.L.G..FSDPVQGD.IS-----GNF.ISGK.M.SAS.FGMFSA.....----EKNP  61
18  .--NCK..F-ITTTL.S.MS.L.G..FSDAVQND.VG-----GNF.ISGK.V.SVS.FGVFSA.Q----ERNT  61
19  .--NYK.VF-ITSALIS...SSL.GV.FSDPA-GSGIN-----GNF.ISGK.M.SAS.FGVFSA.....----ERNT  60
20  .--NYK...-VGVALAT.LS.L.DN.FSDA-----NVPEGRKGF..T...VGVPNF.NFSAE.TL----PGL  61
21  --RYKDFSN--NIDVIIGT.VG-----CFSGS.DVSD-SLNSRLKPVFL..S..LSAPLF.SFS.G.TYR----INGVK-  66
```

Fig. 2A

```
 1  TVEVFGLKKDLLNDLLTGIKDNT------------NFNIKYNPYYENNRLGFSGIFGYYNKFRIESELSYETFHIKNNG  127
 2  RSTIPHMVQSVAQGT.PPEALEELADGKFPEGYLY.T.P...T.KK.L..AG.VI..S-TTH..V.V.AF.DK.NLTAPA  148
 3  ---I...A.ITA.TKFDTL.E.FSFSPL-------HQTDS.KS-.Q.DL..IGLSV.L-FV.S.....F.GA.KN.NT.RLA  128
 4  ------.SSEEFKKIKANLN.ILKSNA---------.LQFQD.TTS...TI...-FS.GL.L.A.GC.QE.NV..SN    130
 5  V.DLI..TT.VTYIT-----EHILRDNT-------K...TH.IAKFK..FIN..SAI...SGQGP.L.I.S..GD.DVV.YK 131
 6  .IQLV.Y..SASSI---------DPNTYS------..QGP.TVTFQD.AAS...AI...S.PESL.L.L.G...K.DV.DPK 130
 7  .K.LL..A..IKSIT--------DITTNK------K....P..TKFQD.AVS..AAV..ISQDSP.V.V.W...E.DV..P. 132
 8  NIQLI..RHNAISTS--------LNINT-------D....P.KVTFQ..ITS..AI..SDPTGA.F.L.G...E.DVTDP. 128
 9  .TQLV......ISVIG------NSNITTYT-----..FP.IAEFQD.AIS...AI..L.SE....V.A...E.DV..PE  133
10  .KILIA....INSLEVNADASQGISHPG-------.T.P.IAAF.D.AFN.N.AI.-ITEGL...I.G...E.DA..P.  135
11  .QQLVA....IDSVDISTNA.SGINNPQ-------.T.P.I.KFQD.AAS...AL.FF.ARGL.L.M.G...E.DV..P. 136
12  .KYLAA....INSVEFDDSVTAGISYPL-------.STP.IAVFQD.ISN.N.AI..TFVEGP...I.G...E.DV.DP. 137
13  .KQLIA....INSVAVGSNATTGISNPG-------.T.P.TAEFQD.VAN.N.AV..SFPDSL...I.GFH.K.DV..P. 137
14  .KK.......-----GD.AQSANFNRT--------DPALEFQN---.LIS...SI..AM-DGP...L.AA.QK.DA..PD 135
15  ..ALY....Q.WNG-VSASSHADADFNNK------GYSF..EN---.PF...A.AI..SM-GGP...F.V.....DV..Q. 130
16  ..G....IEQ.WDRCVISRTTLSDIFTVP------YSF..EN---.LFS..A.AI..SM-DGP...L.V.....A.DV..Q. 131
17  ..ALY....Q.WEG-ISSSSHNDNHFNNK------GYSF..EN---.PF...A.AI..SM-GGP.V.F.V.....DV..Q. 130
18  .IG......Q.WDGSTISKNSPENTFNVP------YSF..EN---.PF...A.AV..LM-NGP...L.M.....DV..Q. 131
19  ..G......QNWDGSAISNSSP.DVFTVS------YSF..EN---.PF...A.AI..SM-DGP...L.V.....DV..Q. 130
20  .KSI.A.GL.----KSS.S.HAGFTQA--------Y.PT.AS---.-FA..G.VI..V-ND..V.F.GA..N.EPERQ-  123
21  .DR.V....S.---I..DAD.AMKDFNNF------..SEE.V.K.D..IF.L.F....SFRN-L.V.L.G..KK.DVIDTR 136
```

Fig. 2B

```
1    --YKRI-DCEKHFALAKEISGGSNNPANNK----------------YVTLINNGISLTSALINVCYDVDGLKHN-IITYSCL..   189
2    G-.LH-KNFYEY...TTMDTKHPHQSAEDK---------------YYMK.T..T.SPFI.A..FILK.TRNVAP.L..       213
3    -R..S-K.GY.Y..IPRKSEH.FLDNT------------------FG.TVAK....II.NI..L.SETKYKS---FTP.I.I   188
4    N-SLI.SSN--.YHSRIHDEN------------------------AITT..KL.IA.IMV.T...ISINNTS-..VP.L.T   183
5    N-.A-VQ.VNRY...VR.KN.SNFS.KPHETSQPSDSNPKKSF-.TLMK...VFVA.VI..G...FSFNNTT-..SP.V.I   207
6    D-.S-AK.AFRF...RNT.T--TV.DAQ.----------------Y---TVMK...L.VA.IM..G...LSFNNLV-VSP.I.A 191
7    N-.V-VSEAFRYI..RG.DNLQKY.ET..----------------Y---.VIK...L.VA.II..G...FSLNNLK-VSP.I.V 195
8    D-CL-.K.TYRY...RNP..-SS.TS.N-----------------Y--TVMR.D.V.I..VIF.G...IFLKDLE-VSP.V.V 189
9    G--.SAT.AYRY...RAMD.T----.KSSPD--DTRKF-------Y--TVMR.D.L.IS.VM..G...NFTLDDIP-VVP.V.A 197
10   G-.G-LN.AFRY...RDMESNKFQ.KAQSSQ------KVF-HTVMKSD.L.II.IMG.GW.FSSDNLL-VSP.I.G       203
11   G-.TKVK.AYRY...R.MQS.QTC.KHKETS---GIQPHGIY-HTVMR.D.V.IS.VI..G..NFTLSNLP-.SP.M.V   210
12   R-.TE.Q.AYRY...RD.DSIPTS.K.RTSHD--GNSSYKVY-HTVMK.E.L.II.IMV.G...FSSDNLS-.LP.V.G   212
13   G-.TQVK.AYRY...RDLKD.FFE.KAEDTG------------VY-HTVMK.D.L.IL.TMV.....FSVDELP-VLP.I.A 205
14   NNDTNSG.YY.Y.G.SR.DAIADK-----K---------------.V.K.E..TFM.LMV.T...ITAEGVP-F.P.A.A   195
15   GN..NDAH--RYC..DRKA.ST--N.TASH---------------.L.K.E.LLDI.LML.A...VSEGIP-FSP.I.A   191
16   NN..NEAH--RYY..SHLLGTETQIDGAGSA--------------.S.F..E.LLDK.FML.A...ISEGIP-FSP.I.A   195
17   NN..NDAH--RYC..GQQDNS..--IPKTSK--------------.L.KSE.LLDI.FML.A...IINESIP-LSP.I.A   191
18   NN..NDAH--.YY..TH--NS.GKLSNAGDK--------------F.F.K.E.LLDI.LML.A...ISEGIP-FSP.I.A   193
19   NN..NEAH--RYC..SH--NSAADMSSASNN--------------F.F.K.E.LLDI.FML.A....V.EGIP-FSP.I.A   192
20   -W.PEGGESH.F...SR.STVQD.----K----------------FIV.E.D.VIDK.LNV.F...IAHGSIP-LAP.M.A   182
21   NHL--VDNNYR.I..VR----------------------------SNPPTLYD.FV.K.D.VEFY.TIL.I...FAVDT---.VPF..V 193
```

Fig. 2C

```
 1  GFGVDTIDFLSKYTTKFSYQGKLGASYTVSPQVSVFIEGYYHGLFGKKFEKIPVNYPCDYPSPTPP--NSKPHVHTTALA  267
 2  V.GNF...DQVSF.A..A.V.I..F..NIAF..D.SF..HLNNQ.SDS...-V.-------SSSGFP.IS.            280
 3  V.G.F.EIFDVMRI..A...V.V..PITSKLILS.N.Q..KVI.N...LL..YQ.VELKRLVTNKTSKDIDQDV..SL    268
 4  I.E.LVGLFNTIHF..LA....V.M..LINNNILL.SDI...KVM.NR.KNLY...MQYVAD--PNISEETIPI.       254
 5  V.G.F.FEVMHI..AC.S.V.I..PI..SITI.ADAH..KVINN...NNLH------VKYSYE--LKNSPTI.S.T.      278
 6  I.E.F.FDTLHI..LA......I..YFF.KIN..AG.....RVI.N..KNLN-------VNHVVT--PDEFPKA.S.V.   262
 7  .G.I.E.F.AVSF..A.....V.I..PLFSNMII.AD.....KVI.N..NNLN------VQHVVS--LNSHPKS.F.V.   266
 8  V.G.F.E.FDALHI..LA......IN.HL.T.A....D.....KVI.NQ.NNLN------VQHVAS--TDFGP--VY.V.  258
 9  I.G.F.E.FNDLHV..AH......V.I..SI..E..L.LN...KVT.NR.KNLH------VQHVSD--L.DAPKF.S.V.  268
10  I...A.E.FDALHI.LACPS...IT.QL.YNI.L.AV.F..QVI.NQ.RNLN------VQHVAE--LNDAPKV.S.V.    274
11  M.I.A.Q.FDSLHI..AH.S...IT.PL.SN.HL.ADS...KVI.N...KNLR------VQHVYE--LQQVPKV.S.V.   281
12  I..NA.E.FDALHV..AC.....IT.PL.SN..L.AG.....QVM.NQ.KNLN------VQHVAF--LNDAPKV.S.V.   283
13  M.INA.E.FDALHV..A......I..QLFTK.NL.LD.....QVI.NQ.KNLN------VNHVYT--LKESPKV.S.V.   276
14  V.A.L.NVFKDFNL........I..PIT.E..A..G......VI.NN.N....------IT.VVL--EGA.QTTS-..V   266
15  V.T.L.SMFEAINP..I......L..SIN.EA......VG.HF.KVA.NE.RD.ST---LKAFAT--P.SAATPDL.TV   263
16  I.I.LVSMFEAINP..I......L..PI..EA......G.HF.KVI.NE.RD..T---MI.SES--ALAGKGNYP.IV   267
17  V.T.L.SMFEATNP..I......L..SIN.EA......G.HF.KVI.NE.RD..T---LKAFVT--S.--ATPDL.IV   261
18  V.T.L.SMFEAINP..I......L..SI..EA......VG.HF.KVI.NE.RD..A---MI.STS--TLTGN-.F-TIV  263
19  I.T.LVSMFEATNP..I......L..SI..EA......G.HF.KVI.NE.RD..T---II..GS--TLAGKGNYP.IV   264
20  V.A.Y.K..GISLP....V.F.VN.P..VN.ML.GG....KVI.NRY.RVEI-----AYHPAT--LTNVPKT.S.S.     254
21  I.E.I.KIFDSIRF.P.FNS..IN.LM.QDMLL.FDV...RVV.NEYNN..Q.------V--SLPNPLNISTA.        262
```

Fig. 2D

| | | | |
|---|---|---|---|
| 1 | MLSIGYYGGSIGIKFI--L | 284 | (SEQ ID NO. 1) |
| 2 | KFNANFLTS....R...-S | 297 | (SEQ ID NO. 2) |
| 3 | T.NLEHFSSE..LS...F | 285 | (SEQ ID NO. 3) |
| 4 | K.D...F.SE...R.MFN | 272 | (SEQ ID NO. 4) |
| 5 | K.N.E.F..EV.MR..F | 295 | (SEQ ID NO. 5) |
| 6 | T.NVA.F..EA.V..TF | 279 | (SEQ ID NO. 6) |
| 7 | T.NVE.F.SEF.L...F | 283 | (SEQ ID NO. 7) |
| 8 | T.N...F.E...RLTF | 275 | (SEQ ID NO. 8) |
| 9 | T.NV..F..E..VR..F | 285 | (SEQ ID NO. 9) |
| 10 | T.NV..F.AEV.VR..F | 291 | (SEQ ID NO. 10) |
| 11 | T.D...F..EV.VR..L | 298 | (SEQ ID NO. 11) |
| 12 | T.D...F..E..ARL.F | 300 | (SEQ ID NO. 12) |
| 13 | T.D.A.F..EV..R.TF | 293 | (SEQ ID NO. 13) |
| 14 | TIDT..F..EV.VR.TF | 283 | (SEQ ID NO. 14) |
| 15 | T..VCHF.VEL.GR.NF | 280 | (SEQ ID NO. 15) |
| 16 | T.DVF.F.IEL.GR.NFQ. | 286 | (SEQ ID NO. 16) |
| 17 | T..VCHF.IEL.GR.NF | 278 | (SEQ ID NO. 17) |
| 18 | T..VCHF.VEL.GR.NF | 280 | (SEQ ID NO. 18) |
| 19 | I.DVCHF.IEL.GR.AF | 281 | (SEQ ID NO. 19) |
| 20 | T.DTD.F.WEV.MR.T--. | 271 | (SEQ ID NO. 20) |
| 21 | K.DME.F.AE....-VF-V | 279 | (SEQ ID NO. 21) |

Fig. 2E

EHRLICHIA CHAFFEENSIS 28 KDA OUTER MEMBRANE PROTEIN MULTIGENE FAMILY

CROSS-REFERENCE TO RELATED APPLICATION

This is a divisional application of U.S. Ser. No. 09/846,808, filed May 1, 2001, now abandoned, which claims benefit of provisional U.S. Ser. No. 60/201,035, filed May 1, 2000, now abandoned.

FEDERAL FUNDING LEGEND

This invention was produced in part using funds obtained through a grant from the National Institute of Allergy and Infectious Disease (AI31431). Consequently, the federal government has certain rights in this invention.

BACKGROUND OF THE INVENTION

1. Field of the Invention

The present invention relates generally to the fields of microbiology, bacteriology and molecular biology. More specifically, the present invention relates to the molecular cloning and characterization of the *Ehrlichia chaffeensis* 28 kD outer membrane protein multigene family.

2. Description of the Related Art

*Ehrlichia* are small, obligatory intracellular, gram negative bacteria which reside in endosomes inside host cells. *Ehrlichiae* usually cause persistent infection in their natural animal hosts (Andrew and Norval, 1989, Breitschwerdt et al., 1998, Dawson et al., 1994, Dawson and Ewing, 1992, Harrus et al., 1998, Telford et al., 1996). Persistent or prolonged *Ehrlichia* infections in human hosts have also been documented (Dumler et al., 1993, Dumler and Bakken, 1996, Horowitz, et al., 1998, Roland et al. 1994). The persistent infection may be caused by the antigenic variation of the *Ehrlichia* omp-2 and p28 outer membrane protein family due to differential expression or recombination of the msp-2 multigene family (Palmer et al., 1994, Palmer et al., 1998) or the p28 multigene family (Ohashi et al., 1998b, Reddy et al., 1998, Yu et al., 1999b).

The omp-2 and p28 are homologous gene families coding for outer membrane proteins. The msp-2 multigene family has been identified in *A. marginale* (Palmer et al., 1994), *A. ovina* (Palmer et al., 1998), and the human granulocytotropic ehrlichiosis agent (Ijdo et al., 1998, Murphy et al., 1998). The p28 multigene family has been found in *E. canis* group *ehrlichiae* including *E. canis, E. chaffeensis*, and *E. muris* (McBride et al., 1999a, 1999b, Ohashi et al., 1998a, 1998b, Reddy et al., 1998, Yu et al., 1999a, 1999b). The map-1 multigene family found in *Cowdria ruminantium* is more closely related to the p28 multigene family than to the msp-2 multigene family, both in sequence similarity and gene organization (Sulsona et al., 1999, van Vliet et al., 1994). The msp-2 genes are dispersed in the genome whereas the p28/map-1 genes are located in a single locus.

To elucidate the mechanism of the host immune avoidance involving the multigene family, the critical questions that remain to be answered are how many genes are present in each multigene family and which genes are silent or active. *E. chaffeensis* is the pathogen of an emerging disease, human monocytotropic ehrlichiosis. Recent studies have found seven homologous polymorphic p28 genes in *E. chaffeensis* which encode proteins from 28 to 30-kDa (Ohashi et al., 1998b, Reddy et al., 1998). The seven sequenced p28 genes were located in three loci of the *E. chaffeensis* genome. The first locus, omp-1 contained six p28 genes. One gene was partially sequenced (omp1-a) and five genes were completely sequenced (omp-1b, -1c, -1d, -1e, and -1f) (Ohashi et al., 1998b). The second locus contained a single p28 gene (Ohashi et al., 1998b, Yu et al., 1999b). The third locus contained five p28 genes (ORF 1 to 5). The first four open reading frames overlapped with the DNA sequences from omp-1 c to omp-1f and the fifth open reading frame overlapped with the single gene in the second locus. Therefore, the three loci could be assembled into a single locus (Reddy et al., 1998).

The prior art is deficient in the lack of the knowledge of many of the sequences of the genes in the p28 multigene family of *E. chaffeensis*. The present invention fulfills this long-standing need and desire in the art.

SUMMARY OF THE INVENTION

The 28-kDa outer membrane proteins (P28) of *Ehrlichia chaffeensis* are encoded by a multigene family. The p28 multigene family of *E. chaffeensis* is located in a single locus, which is easy to sequence by genome walking. The purpose of this study was to determine all the p28 gene sequences and their transcriptional activities. There were 21 members of the p28 multigene family located in a 23-kb DNA fragment in the *E. chaffeensis* genome. The p28 genes were 816 to 903 nucleotides in size and were separated by intergenic spaces of 10 to 605 nucleotides. All the genes were complete and were predicted to have signal sequences. The molecular masses of the mature proteins were predicted to be 28- to 32-kDa. The amino acid sequence identity of the P28 proteins was 20-83%. Ten p28 genes were investigated for transcriptional activity by using RT-PCR amplification of mRNA. Six of 10 tested p28 genes were actively transcribed in cell culture grown *E. chaffeensis*. RT-PCR also indicated that each of the p28 genes was monocistronic. These results suggest that the p28 genes are active genes and encode polymorphic forms of the P28 proteins. In addition, the P28s were divergent among separate isolates of *E. chaffeensis*. The large repertoire of the p28 genes in a single ehrlichial organism and antigenic diversity of the P28 among the isolates of *E. chaffeensis* suggest that P28s may be involved in immune avoidance.

The present invention describes the molecular cloning, sequencing, characterization, and expression of the multigene locus of P28 from *Ehrlichia chaffeensis*. The present invention describes a number of newly described genes for P28 proteins including proteins having amino acid sequences selected from the group consisting of SEQ ID No. 1, SEQ ID No.2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No 11, SEQ ID No. 12, SEQ ID No. 13, SEQ ID No. 20 and SEQ ID No. 21. These P28 genes are contained in a single 23 kb multigene locus of *Ehrlichia chaffeensis*. The novel part of this locus are described in GenBank accession number AF230642 and GenBank accession number AF230643.

The instant invention is also directed to DNA encoding a P28 protein selected from those described above. This DNA may consist of isolated DNA that encodes a P28 protein; isolated DNA which hybridizes to DNA encoding an isolated P28 gene, and isolated DNA encoding a P28 protein which differs due to the degeneracy of the genetic code.

The instant invention is also directed to a vector comprising a P28 gene and regulatory elements necessary for expression of the DNA in a cell. This vector may be used to transfect a host cell selected from group consisting of bacterial cells, mammalian cells, plant cells and insect cells. E. coli is an example of a bacterial cell into which the vector may be transfected.

The instant invention is also directed to an isolated and purified Ehrlichia chaffeensis P28 surface protein selected from those described above including those with amino acid sequences SEQ ID No. 1, SEQ ID No.2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No 11, SEQ ID No. 12, SEQ ID No. 13, SEQ ID No. 20 and SEQ ID No. 21.

The instant invention also describes an antibody directed against one of these P28 proteins. This antibody may be a monoclonal antibody.

The novel P28 proteins of the instant invention may be used in a vaccine against *Ehrlichia chaffeensis.*

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the scheme of sequencing the p28 gene locus by genome walking and the organization of the p28 genes. Three loci of p28 genes previously sequenced were aligned and assembled into a single contiguous sequence. Initial primers (arrow heads) were designed near the 5' and 3' ends of the contiguous sequence to walk the genome. The block arrows represented the positions and the directions of the p28 genes. The scale indicated the nucleotides in kilobases.

FIG. 2 shows a clustal alignment of the amino acid sequences of the *E. chaffeensis* Arkansas strain P28s (1-21). P28-1 was used as consensus sequence. Dots represented residues identical to those of the consensus sequence. Gaps represented by dash lines were introduced for optimal alignment of the DNA sequences. The hypervariable regions were underlined.

FIG. 3 shows the phylogenetic relationships of the P28s (1-21. The number on the branch indicated the bootstrap values.

FIG. 4 shows Southern blotting. Two bands of 17.6 and 5.3 kb were detected by a p28 gene probe on Cla I restriction endonuclease digested *E. chaffeensis* genomic DNA (lane E). M: molecular weight marker.

FIG. 5 shows RT-PCR amplification of the mRNA of *E. chaffeensis* p28 genes (RT-PCR). In the PCR controls, reverse transcriptase was omitted. The numbers of each lane indicated the p28 genes. M represents a molecular weight marker.

DETAILED DESCRIPTION OF THE INVENTION

The following abbreviations may be used herein: BCIP/NBT-5-bromo-4-chloro-3-indolylphosphate/nitrobluetetrazolium substrate; ATP—adenosine triphosphate; DNA—deoxyribonucleic acid; E—*Ehrlichia*; kDa—kilodalton; mRNA—messenger ribonucleic acid; ORF—open reading frame; P28—28-kDa outer membrane proteins; PCR—polymerase chain reaction; RT-PCR—reverse transcriptase-polymerase chain reaction.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A DNA "coding sequence" is a double-stranded DNA sequence that is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically. A "primer" is capable of acting as a point of initiation of synthesis when placed under conditions in which synthesis of a primer extension product, which is complementary to a nucleic acid strand, is induced (i.e., in the presence of nucleotides and an inducing agent such as a DNA polymerase and at a suitable temperature and pH). The primer may be either single-stranded or double-stranded and must be sufficiently long to prime the synthesis of the desired extension product in the presence of the inducing agent. The exact length of the primer will depend upon many factors, including temperature, source of primer and intended use. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous' region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally occurring mutational events do not give rise to a heterologous region of DNA as defined herein.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

As used herein, the term "host" is meant to include not only prokaryotes but also eukaryotes such as yeast, plant and animal cells. A recombinant DNA molecule or gene which encodes a 28-kDa immunoreactive protein of *Ehrlichia chaffeensis* of the present invention can be used to transform a host using any of the techniques commonly known to those of ordinary skill in the art. Especially preferred is the use of a vector containing coding sequences for a gene encoding a 28-kDa immunoreactive protein of *Ehrlichia chaffeensis* of the present invention for purposes of prokaryote transformation.

Prokaryotic hosts may include *E. coli*, *S. typhimurium*, *Serratia marcescens* and *Bacillus subtilis*. Eukaryotic hosts include yeasts such as *Pichia pastoris*, mammalian cells and insect cells.

In general, expression vectors containing promoter sequences which facilitate the efficient transcription of the inserted DNA fragment are used in connection with the host. The expression vector typically contains an origin of replication, promoter(s), terminator(s), as well as specific genes that are capable of providing phenotypic selection in transformed cells. The transformed hosts can be fermented and cultured according to means known in the art to achieve optimal cell growth.

By "high stringency" is meant DNA hybridization and wash conditions characterized by high temperature and low salt concentration, e.g., wash conditions of 65° C. at a salt concentration of approximately 0.1×SSC, or the functional equivalent thereof. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

By "substantially pure DNA" is meant DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences. It also includes a recombinant DNA that is part of a hybrid gene encoding additional polypeptide sequence, e.g., a fusion protein.

The identity between two sequences is a direct function of the number of matching or identical positions. When a subunit position in both of the two sequences is occupied by the same monomeric subunit, e.g., if a given position is occupied by an adenine in each of two DNA molecules, then they are identical at that position. For example, if 7 positions in a sequence 10 nucleotides in length are identical to the corresponding positions in a second 10-nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

A "vector" may be defined as a replicable nucleic acid construct, e.g., a plasmid or viral nucleic acid. Vectors may be used to amplify and/or express nucleic acid encoding a 28-kDa immunoreactive protein of *Ehrlichia chaffeensis*. An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences which control the termination of transcription and translation. Methods, which are well known to those skilled in the art, can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

By a "substantially pure protein" is meant a protein that has been separated from at least some of those components that naturally accompany it. Typically, the protein is substantially pure when it is at least 60%, by weight, free from the proteins and other naturally occurring organic molecules with which it is naturally associated in vivo. Preferably, the purity of the preparation is at least 75%, more preferably at least 90%, and most preferably at least 99%, by weight. A protein is substantially free of naturally associated components when it is separated from at least some of those contaminants that accompany it in its natural state. Thus, a protein that is chemically synthesized or produced in a cellular system different from the cell from which it naturally originates will be, by definition, substantially free from its naturally associated components. Accordingly, substantially pure proteins include eukaryotic proteins synthesized in *E. coli*, other prokaryotes, or any other organism in which they do not naturally occur.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

A protein may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 ml of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

As is well known in the art, a given polypeptide may vary in its immunogenicity. It is often necessary therefore to couple the immunogen (e.g., a polypeptide of the present invention) with a carrier. Exemplary and preferred carriers are keyhole limpet hemocyanin (KLH) and human serum albumin. Other carriers may include a variety of lymphokines and adjuvants such as IL2, IL4, IL8 and others.

Means for conjugating a polypeptide to a carrier protein are well known in the art and include glutaraldehyde, m-maleimidobenzoyl-N-hydroxysuccinimide ester, carbodiimide and bis-biazotized benzidine. It is also understood that the peptide may be conjugated to a protein by genetic engineering techniques that are well known in the art.

As is also well known in the art, immunogenicity to a particular immunogen can be enhanced by the use of non-specific stimulators of the immune response known as adjuvants. Exemplary and preferred adjuvants include complete BCG, Detox, RIBI (Immunochem Research Inc.), ISCOMS and aluminum hydroxide adjuvant (Superphos, Biosector).

As used herein the term "complement" is used to define the strand of nucleic acid which will hybridize to the first nucleic acid sequence to form a double stranded molecule under stringent conditions. Stringent conditions are those that allow hybridization between two nucleic acid sequences with a high degree of homology, but precludes hybridization of random sequences. For example, hybridization at low temperature and/or high ionic strength is termed low stringency and hybridization at high temperature and/or low ionic strength is termed high stringency. The temperature and ionic strength of a desired stringency are understood to be applicable to particular probe lengths, t o the length and base content of the sequences and to the presence of formamide in the hybridization mixture.

As used herein, the term "engineered" or "recombinant" cell is intended to refer to a cell into which a recombinant gene, such as a gene encoding an *Ehrlichia chaffeensis* antigen has been introduced. Therefore, engineered cells are distinguishable from naturally occurring cells that do not contain a recombinantly introduced gene. Engineered cells are thus cells having a gene or genes introduced through the hand of man. Recombinantly introduced genes will either be in the form of a cDNA gene, a copy of a genomic gene, or will include genes positioned adjacent to a promoter not naturally associated with the particular introduced gene. In addition, the recombinant gene may be integrated into the host genome, or it may be contained in a vector, or in a bacterial genome transfected into the host cell.

The following examples are given for the purpose of illustrating various embodiments of the invention and are not meant to limit the present invention in any fashion.

EXAMPLE 1

*Ehrlichia* spp

*Ehrlichia chaffeensis* (Arkansas strain) was obtained from Jacqueline Dawson (Centers for Disease Control and Prevention, Atlanta, Ga.). *Ehrlichiae* were cultivated in DH82 cells, a canine macrophage-like cell line. DH82 cells were harvested with a cell scraper when 100% of cells were infected with ehrlichiae. The cells were centrifuged at 17,400×g for 20 min. The pellets were disrupted twice with a Braun-Sonic 2000 sonicator at 40 W for 30 sec on ice. *Ehrlichia* were then purified by using 30% Percoll gradient centrifugation (Weiss et al, 1989).

EXAMPLE 2

PCR Amplification of the p28 Multigene Locus

*Ehrlichia chaffeensis* genomic DNA was prepared by using an IsoQuick Nucleic Acid Extraction Kit (ORCA Research Inc., Bothell, Wash.) according to the instructions of the manufacturer. The unknown sequences of the p28 multigene locus were amplified by PCR using the Universal GenomeWalker Kit (Clontech Laboratories, Inc., Palo Alto, Calif.). Briefly, the *E. chaffeensis* genomic DNA was digested respectively with Dra I, EcoR V, Pvu II, Sca I, and Stu I. The enzymes were chosen because they generated blunt ended DNA fragments to ligate with the blunt-end of the adapter. The digested *E. chaffeensis* genomic DNA fragments were ligated with a GenomeWalker Adapter, which had one blunt end and one end with 5' overhang. The ligation mixture of the adapter and *E. chaffeensis* genomic DNA fragments was used as template for PCR. Initially, the p28 gene-specific primer amplified the known DNA sequence and extended into the unknown adjacent genomic DNA and the adapter 5'overhang, which is complementary to the adapter primer. In the subsequent PCR cycles, the target DNA sequences were amplified with both the p28 gene-specific primer and the adapter primer.

EXAMPLE 3

DNA Sequencing

The PCR products were purified by using a QIAquick PCR Purification Kit (QIAGEN Inc., Santa Clarita, Calif.) and were sequenced directly using PCR primers when a single clear band was observed on the ethidium-bromide stained agarose gel. If multiple bands appeared, the DNA band of interest was excised from the gel, and the DNA was extracted from the gel using the Gel Extraction Kit (QIAGEN Inc., Santa Clarita, Calif.). The gel-purified DNA was cloned into the Topo TA cloning vector (Invitrogen, Inc., Carlsbad, Calif.) according to the instructions of the manufacturer. A High Pure Plasmid Isolation Kit (Boehringer Mannheim Corp., Indianapolis, Ind.) was used to purify the plasmids. An ABI Prism 377 DNA Sequencer (Perkin-Elmer Applied Biosystems, Foster City, Calif.) was used to sequence the DNA in the Protein Chemistry Laboratory of the University of Texas Medical Branch.

EXAMPLE 4

Gene Analysis

DNA sequences and deduced amino acid sequences were analyzed using DNASTAR software (DNASTAR, Inc., Madison, Wis.). The signal sequence of the deduced protein was analyzed by using the PSORT program, which predicts the presence of signal sequences (McGeoch, 1985, Von Heijne, 1986) and detects potential transmembrane domains (Klein, 1985). Phylogenetic analysis was performed by the maximum parsimony method of the PAUP 4.0 software (Sunderland Mass.: Sinauer Associates, 1998). Bootstrap values for the consensus tree were based on analysis of 1000 replicates.

EXAMPLE 5

DNA Sequence Accession Numbers

The DNA sequences of the *E. chaffeensis* p28 genes were assigned GenBank accession numbers: AF230642 for the DNA locus of the p28-1 to p28-13 and AF230643 for the DNA locus of p28-20 and p28-21.

EXAMPLE 6

Reverse Transcriptase PCR (RT-PCR)

Total RNA of *E. chaffeensis*-infected DH82 cells was isolated using RNeasy Total RNA Isolation Kit (Qiagen Inc., Santa Clarita, Calif.). The p28 gene mRNA (0.5 μg total RNA) was amplified using a Titan One Tube RT-PCR System (Roche Molecular Biochemicals, Indianapolis, Ind.) according to the manufacturer's instructions. Gene-specific primer pairs used in the RT-PCR reaction were listed in Table 1. A negative control that included all reagents except reverse transcriptase was included to confirm that genomic DNA was not present in the total RNA preparation. The thermal cycling profile consisted of reverse transcription at 50° C. for 30 min, amplification for 30 cycles at 94° C. for 2 min, 50° C. for 1 min, and 68° C. for 1 min, and an elongation step at 68° C. for 7 min.

EXAMPLE 7

Southern Blotting

The DNA sequences of the p28 multigene locus were analyzed for the presence of restriction sites using a Mapdraw program (DNASTAR, Inc., Madison, Wis.). *Ehrlichia chaffeensis* genomic DNA was digested by restriction endonuclease Cla I. The DNA was separated using a 0.8% agarose gel. DNA was blotted onto nylon membranes by capillary transfer. The probe was DNA-amplified from the p28 multigene locus by using PCR and was labeled with digoxigenin-11-dUTP using a DIG DNA Labeling Kit (Roche Molecular Biochemicals, Indianapolis, Ind.). The probe corresponded to the nucleotides from 8900 to 10620 of the locus, which included the 3' end of p28-7, the entire gene of p28-8, the 5' end of p28-9, and the intergenic sequences between the three genes. DNA hybridization was performed at 42° C. overnight in the Eazy Hybridization Buffer (Roche Molecular Biochemicals, Indianapolis, Ind.). The DNA probes were detected using the calorimetric reagent (BCIP/NBT) following the instructions of the manufacturer (Roche Molecular Biochemicals, Indianapolis, Ind.).

EXAMPLE 8

PCR Amplification of the p28 Multigene Locus

The sequences of three p28 gene loci were obtained from GenBank (accessions: AF021338, AF062761, and AF068234) (Ohashi et al., 1998b, Reddy et al., 1998, Yu et al., 1999b) and were assembled into a single contiguous DNA sequence which contained seven p28 genes with the first one incomplete. Gene-specific primers to the partial gene (primer 1a-r1 and primer 1a-r2) and the DNA sequence

TABLE 1

Gene-specific primers for RT-PCR

| Gene | Sequences of forward (f) and reverse (r) primers | | Product length (bp) |
|---|---|---|---|
| p28-10 | (f) ACG TGA TAT GGA AAG CAA CAA GT | (SEQ ID No. 22) | 384 |
|  | (r) GCG CGG AAA TAT CCA ACA | (SEQ ID No. 23) |  |
| p28-11 | (f) GGT CAA ACT TGC CCT AAA CAC A | (SEQ ID No. 24) | 406 |
|  | (r) ACT TCA CCA CCA AAA TAC CCA ATA | (SEQ ID No. 25) |  |
| p28-12 | (f) CTG CTG GCA TTA GTT ACC C | (SEQ ID No. 26) | 334 |
|  | (r) CAT AGC AGC CAT TGA CC | (SEQ ID No. 27) |  |
| p28-13 | (f) ATT GAT TGC CTA TTA CTT GAT GGT | (SEQ ID No. 28) | 333 |
|  | (r) AAT GGG GCT GTT GGT TAC TC | (SEQ ID No. 29) |  |
| p28-14 | (f) TGA AGA CGC AAT AGC AGA TAA GA | (SEQ ID No. 30) | 269 |
|  | (r) TAG CGC AGA TGT GGT TTG AG | (SEQ ID No.31) |  |
| p28-15 | (f) ACT GTC GCG TTG TAT GGT TTG | (SEQ ID No. 32) | 371 |
|  | (r) ATT AGT GCT GCT TGC TTT ACG A | (SEQ ID No. 33) |  |
| p28-17 | (f) TGC AAG GTG ACA ATA TTA GTG GTA | (SEQ ID No. 34) | 367 |
|  | (r) GTA TTC CGC TGT TGT CTT GTT G | (SEQ ID No. 35) |  |
| p28-18 | (f) ACA TTT TGG CGT ATT CTC TGC | (SEQ ID No. 36) | 312 |
|  | (r) TAG CTT TCC CCC ACT GTT ATG | (SEQ ID No. 37) |  |
| p28-20 | (f) AAC TTA TGG CTT TCT CCT CCT TTC | (SEQ ID No. 38) | 340 |
|  | (r) TTG CCT GAT AAT TCT TTT TCT GAT | (SEQ ID No. 39) |  |
| p28-21 | (f) ACC AAC TTC CCA ACC AAA ATA ATC | (SEQ ID No. 40) | 421 |
|  | (r) CTG AAG GAG GAG AAA GCC ATA AGT | (SEQ ID No. 41) |  | downstream of the last p28 gene (primers 28f1 and 28f2) were designed from the contiguous sequence for the initial extension of the p28 gene locus of *E. chaffeensis*.

The scheme of PCR-amplification of the p28 multigene locus is illustrated in FIG. 1, and the sequences of the gene specific primers were listed in Table 2. A 1.6-kb DNA fragment was amplified initially from the 5' end of the locus from a Stu I-restriction genomic library by nested PCR using primer 1a-r2. The PCR products were sequenced directly, and a new primer (28r3) was designed from the sequence to further extend the 5' end sequence of the locus. A 4.5-kb DNA fragment (pvu4.5) was amplified from a Pvu II-restriction genomic library by using primer 28r3. The 5' end of the DNA locus was further extended with six additional primer walks by using primers: pvur32, 28r12, 28stur, 28r14, and 28r15. Each primer was designed from the DNA sequences from the preceding PCR product. The 3' end of the locus was initially extended for 1.5-kb by nested PCR using primers 28f1 and 28f2. The 1.5-kb DNA fragment was directly sequenced and used to design a new primer (28f3) to further walk the 3' end of the locus. A 2.8-kb DNA fragment (stu2.8) was amplified from a Stu I-restriction genomic library by using primer 28f3. The pvu4.5, pvu1.8, and stu2.8 DNA fragments were gel-purified and cloned into the Topo TA PCR cloning vector. The DNA in the Topo TA vector was sequenced initially using the M13 reverse and M13 forward primers and extended by primer walking. The sequence on the 5' end of stu2.8 was not readable following M13 forward and reverse primers, possibly due to the secondary structure. Thus, the recombinant Topo TA plasmid containing the stu2.8 DNA was digested with the restriction enzyme Kpn I. A 700-bp fragment of DNA was deleted from the 5' end of the stu2.8 DNA. The plasmid was ligated again, and the insert was sequenced using M13 reverse and M13 forward primers. The rest of PCR products were sequenced directly.

EXAMPLE 9 p28 Gene Family Consists of 21 Homologous but Distinct Genes

The sequences of the DNA fragments were assembled together by using the Seqman program (DNASTAR, Inc., Madison, Wis.) into a 23-kb segment of DNA. There were 21 homologous p28 genes in the DNA locus. The genes were designated as p28-1 to p28-21 according to their positions from the 5' end to the 3' end of the locus (FIG. 1). Most of the genes were tandemly arranged in one direction in the locus, and the last two genes (p28-20 and p28-21) were in the complementary strand. The sizes of the genes ranged from 816 bp to 903 bp while length of the non-coding sequences between the neighboring genes varied from 10 to 605-bp. The intergenic spaces between p28-1 and p28-2 and between p28-6 and p28-7 encoded a 150 amino acid protein and a 195 amino acid protein, respectively, and the two proteins had no sequence similarity to any known proteins.

All the P28s were predicted to have a signal sequence. The signal sequences of P28-1, P28-7, and P28-8 were predicted to be uncleavable. The signal sequences of the rest of the P28s were predicted to be cleavable, and the proteins were predicted to be cleaved from positions varying from position 19 to position 30. The predicted molecular sizes of the mature P28s were from 25.8-kDa to 32.1-kDa. The C-termini and the middle of the proteins were most conserved. There were 4 hypervariable regions in the amino acid sequences of the P28 proteins (FIG. 2). The first hypervariable region was immediately after the signal sequence. No proteins had identical sequences in the hypervariable regions (FIG. 2).

TABLE 2

Primers for genome walking the *E. chaffeensis* p28 multigene locus

| Name | Sequences | | Product length (kb) |
|---|---|---|---|
| 1a-r1[a] | ACC AAA GTA TGC AAT GTC AAG TG | (SEQ ID No.42) | |
| 1a-r2 | CTG CAG ATG TGA CTT TAG GAG ATT C | (SEQ ID No.43) | 1.6 |
| 28r3 | TGT ATA TCT TCC AGG GTC TTT GA | (SEQ ID No.44) | 4.5 |
| pvur32 | GAC CAT TCT ACC TCA ACC | (SEQ ID No.45) | 1.8 |
| 28r10 | ATA TCC AAT TGC TCC ACT GAA A | (SEQ ID No.46) | 1.5 |
| 28r12 | CTT GAA ATG TAA CAG TAT ATG GAC CTT GAA | (SEQ ID No.47) | 2.2 |
| 28stur | TGT CCT TTT TAA GCC CAA CT | (SEQ ID No.48) | 1:5 |
| 28r14 | TTC TGC AGA TTG ATG TGG ATG TTT | (SEQ ID No.49) | 4.7 |
| 28r15 | TGC AGA TTG ATG TGG ATG TTT | (SEQ ID No.50) | 1.1 |
| 28f1[b] | GTA AAA CAC AAG CCA CCA GTC T | (SEQ ID No.51) | |
| 28f2 | GGG CAT ATA CCT ACA CCA AAC ACC | (SEQ ID No.52) | 1.5 |
| 28f3 | TAA GAG GAT TGG GTA AGG ATA | (SEQ ID No.53) | 2.8 |

[a] 1a-r1 was outside primer for 1a-r2;
[b] 28f1 was outside primer for 28f2.

EXAMPLE 10

Phylogenetic Relationships of the P28s

Figure 3:
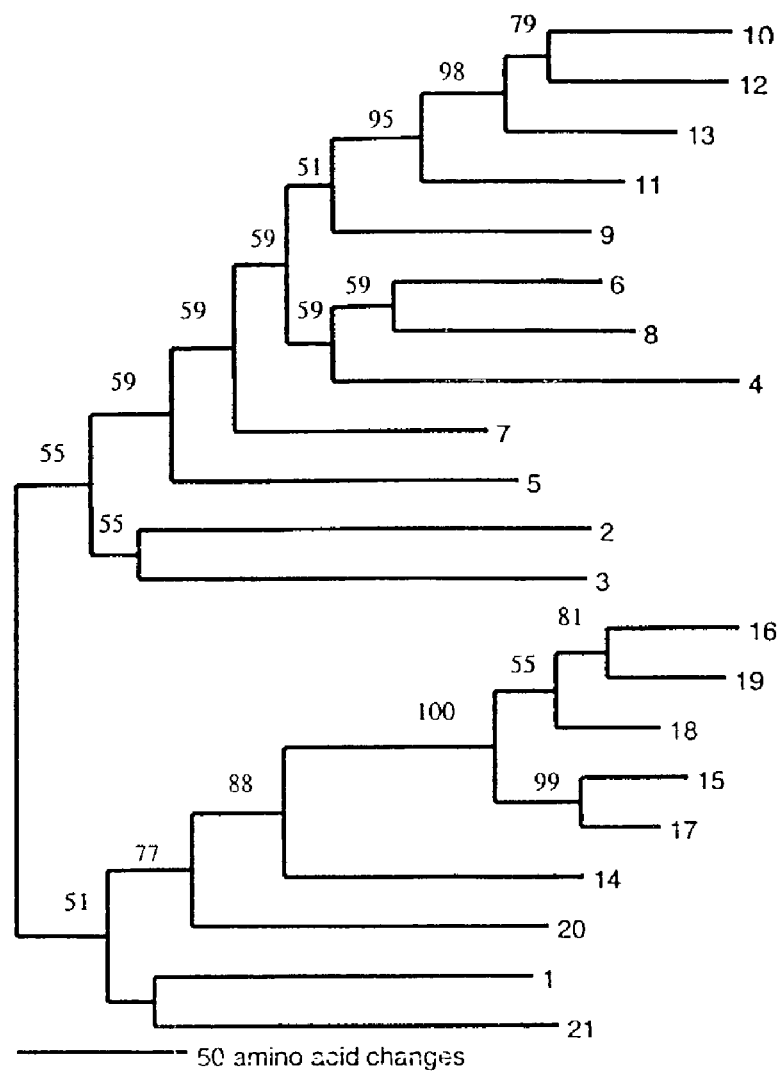

The amino acid sequence identity of the P28s varied from 20% to 83% (FIG. 3). In general, the proteins derived from adjacent genes had higher identities. The P28s having the highest amino acid sequence identities were from P28-16 to P28-19, which were 68.3 to 82.7% identical to each other. The next group with high sequence identity was from P28-7 to P28-13, which were 47.6 to 66.9% identical to each other. The sequence identity among the rest of the E. chaffeensis P28s were from 19.7 to 45.6%. The amino acid sequences of the P28s of E. chaffeensis were highly homologous to the P28 protein families of E. canis and E. muris (McBride et al., 1999a, 1999b, Reddy et al., 1998, Yu et al., 1999a) and the MAP-1 protein family of C. ruminantium (van Vliet et al., 1994, Sulsona et al., 1999). P28-17 of E. chaffeensis was the most conserved protein among the Ehrlichia species. The amino acid sequence of the E. chaffeensis P28-17 was 58% to 60% identical to the P28s of E. canis and 78% to 81% identical to the P28s of E. muris. The P28s of E. chaffeensis also have significant similarity to the MSP-4 protein (Oberle and Barbet, 1993), and the MSP-2 protein families of A. marginale (Palmer et al., 1994) and the MSP-2 of the human granulocytotropic ehrlichiosis agent (Ijdo et al., 1998, Murphy et al., 1998).

EXAMPLE 11 p28 Genes Located in a Single Locus

Figure 4:
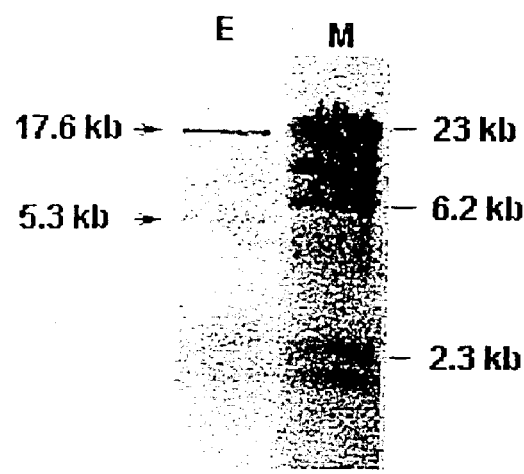

Southern blotting was performed to detect whether all the p28 genes were located on a single locus and whether the whole locus has been sequenced. Cla I restriction endonuclease was predicted to digest the p28 gene locus at three sites generating 5268 bp and 17550 bp DNA fragments. Southern blot using a p28 gene probe demonstrated a strong band of 17.6-kb and a weak band of 5.3-kb in the Cla I-digested E. chaffeensis genomic DNA (FIG. 4). This result indicated that all the p28 genes were located on two Cla I DNA fragments and that all the p28 genes had been sequenced. Sequencing a segment of 2.3 kb DNA upstream of the first p28 gene and a segment of 2 kb downstream of the last p28 gene did not reveal any additional p28 genes.

EXAMPLE 12

Transcriptional Activity of the p28 Multigene Family

Figure 5:
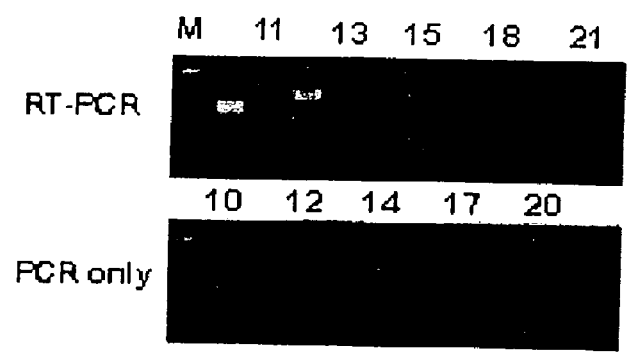

The transcriptional activity was evaluated by RT-PCR for 10 p28 genes including p28-10, p28-11, p28-12, p28-13, p28-14, p28-15, p28-17, p28-18, p28-20, and p28-21 (FIG. 5). These genes were selected for transcriptional analysis because they represented genes tightly clustered together (p28-10 to p28-13), genes with larger intergenic spaces (p28-14 to p28-18), or genes in the complementary strand (p28-20 and p28-21). To ensure the specificity of RT-PCR, each primer pair was designed to be specific for a single p28 gene only. DNA bands of expected size were observed in ethidium-bromide stained agarose gels of the RT-PCR products for the following genes: p28-10, p28-11, p28-12, p28-15, p28-18, and p28-20. No DNA band was detected in ethidium-bromide stained agarose gels of RT-PCR products of the following genes: p28-13, p28-14, p28-17, and p28-21. The rest of the p28 genes were not investigated for their transcription. In the controls, no DNA was amplified from any genes by PCR reactions from which reverse transcriptase was omitted. All the primer pairs produced products of the expected size when using E. chaffeensis genomic DNA as template (data not shown).

EXAMPLE 13

The P28s were Divergent Among the E. chaffeensis Isolates

A p28 gene corresponding to p28-19 of Arkansas strain was sequenced in four additional E. chaffeensis isolates made previously (Yu et al., 1999b). Clustal alignment indicated that none of the P28 genes of the Arkansas strain had identical amino acid sequence with the single sequenced P28 of the four E. chaffeensis isolates. The sequenced P28's from all four isolates were most similar (85-86%) to the P28-19 protein of Arkansas strain. Thus, they were analogs of P28-19 of Arkansas strain.

Discussion

Sequencing of the p28 multigene locus in E. chaffeensis in this study will contribute to the investigation of the origin of the multigene family and the function of the multigenes. Gene families are thought to have arisen by duplication of an original ancestral gene, with different members of the family then diverging as a consequence of mutations during evolution. The most conserved p28 gene among the species of Ehrlichia should be the ancestral gene. E. chaffeensis p28-15 to p28-19 are the genes most similar to the p28 of E. canis and E. muris. Therefore, the p28 genes might have arisen from one of the p28-15 to p28-19 genes. The wide presence of the p28/msp-2 multigenes in the Ehrlichia, Anaplasma, and Cowdria indicate that these organisms are phylogenetically related. The significant sequence identity between the p28 multigene family and the msp-2 multigene family indicates that the two gene families originated from a common ancestor gene.

p28 genes corresponding to the p28-14 to p28-19 were sequenced previously and designated as omp-1b to omp-1f and p28 by Ohashi et al. (1998b) and ORF-1 to ORF-5 by Reddy et al(1998). An alphabetic letter or a number assigned to each gene attempted to indicate the order and position of the genes in the locus. Neither previously assigned letters nor the numbers truly represent the position of the genes in the locus as revealed when it was sequenced completely. Thus, the genes were renamed to best represent the order of the genes in the complete locus. P28 was used as the name of the protein because it accurately describes the molecular mass of an immunodominant protein which was determined before its gene was sequenced (Chen et al., 1994, Yu et al., 1993) and also because the p28 was used to describe its gene name when the first p28 gene was cloned and sequenced (Ohashi et al., 1998b).

Six p28 genes were expressed in cell culture under the particular conditions of the investigation among the 10 genes studied. The genes for which transcription were not detected by RT-PCR are possibly not silent genes either since all the genes were complete genes, i.e., no truncated form of the p28 genes was found. They may be expressed under other conditions. These results were consistent with previous data, which detected multiple bands from 22-29 kDa with a monoclonal antibody (Yu et al., 1993, 1999b). In contrast, a previous study detected only a single p28 gene transcribed in cell culture (Reddy et al., 1998). PCR primer specificity may have contributed to the failure of detection the transcription of multiple genes in the previous study. With the limitation of knowledge of the DNA sequences at that time, although primers were designed to attempt to amplify as many p28 genes as possible, the primer pair (R72 and R74) from the previous study was perfectly matched to only three of the 21 p28 genes (p28-16, -17, and -19). The previous study demonstrated that p28-19 (orf-5) was transcriptionally active and p28-16 and p28-17 were inactive transcriptionally. In the results herein, p28-17 was also transcriptionally inactive. The transcriptional activity of p28-16 and p28-19 was not analyzed. It was possible to detect transcriptional activity in more p28 genes herein because specific primers were used for each p28 gene.

The natural cycles of *Ehrlichia* involve a tick vector and mammalian hosts. Mammals are infected with *Ehrlichia* by the bite of infected ticks, and non-infected ticks acquire *Ehrlichia* by a blood meal from infected animals. *Ehrlichia* are not transovarially transmitted from one generation of ticks to the next (Rikihisa, 1991). Therefore, the mammalian hosts are essential for the maintenance of *Ehrlichia* in nature. Carrier animals serve as the reservoirs for *Ehrlichia* organisms (Swift and Thomas, 1983, Zaugg, et al., 1986). The persistent infection and carrier status indicate that *Ehrlichia* organisms have evolved one or more mechanisms to circumvent the host immune system. Some bacterial pathogens are endowed with sophisticated mechanisms to adapt to a rapidly changing microenviroment in the host. One such system is the reversible switching of the expression of the array of cell surface components exposed to the host defense system.

Homologous recombination of genes in multigene families has contributed to the persistent infection of *Borrelia hermsii* (Schwan and Hinnebusch, 1998) and *Neisseria gonorrhoeae* (Haas and Meyer, 1986). Homologous recombination of the p28 multigenes has been hypothesized (Reddy and Streck, 1999). However, no homologous recombination of p28 genes of *Ehrlichia* has yet been demonstrated. Homologous recombination was not observed in different passages of *E. chaffeensis* or *E. canis*, which have been passaged for several years. The DNA sequences of p28 genes published by different laboratories are identical despite the different passage histories (Ohashi et al., 1998b, Reddy et al., 1998, Yu et al., 1999b), suggesting a lack of recombination as a mechanism of generation of genetic diversity. Moreover, the DNA sequences of five p28 genes in a locus of *E. canis* Jake and Oklahoma isolates are identical despite the temporal and geographic separation of these isolates in nature. The genetic variation of the p28 gene among strains of *E. chaffeensis* is very likely caused by random mutation over a long period of evolution of the gene rather than by homologous recombination.

The p28 genes may be expressed differentially. Neither the *E. chaffeensis* nor the *E. canis* p28 multigenes are one polycistronic gene. Antigenically and structurally distinct msp-2 genes have been expressed in acute *A. marginale* rickettsemia in experimentally infected calf (Eid et al., 1996, French et al., 1999). Protein immunoblotting detected 2-4 proteins in cell culture with a monoclonal antibody to a P28 of *E. chaffeensis* (Yu et al., 1993, 1999b). Although several *E. chaffeensis* p28 genes are transcribed in cell culture, a clone of tick-inoculated *E. chaffeensis* may differentially and sequentially express the p28 multigene family in vivo to evade the host immune system. Different P28 proteins may have similar structure and function for *E. chaffeensis*, but different antigenicity. The hypervariable regions are predicted to contain antigenic epitopes which are surface exposed (Yu et al., 1999b). Thus, the P28s may be essential for immune escape. It was demonstrated that only 40% of convalescent sera of monocytotropic ehrlichiosis patients had antibodies to a P28-19. Patient serum that reacted with the particular P28 of one strain of *E. chaffeensis* might not react with the protein in another strain in which the amino acid sequences of the hypervariable regions differ substantially (Chen et al., 1997, Yu et al., 1999c). The data suggest that the apparent antigenic variability of the P28 may be explained in part by differential expression of the p28 multigene family.

The following references were cited herein:

Andrew, et al., 1989. The carrier status of sheep, cattle and African buffalo recovered from heartwater. Vet. Parasit. 34, 261-266.

Breitschwerdt, et al., 1998. Sequential evaluation of dogs naturally infected with *Ehrlichia canis, Ehrlichia chaffeensis, Ehrlichia equi, Ehrlichia ewingii*, or *Bartonella vinsonii*. J. Clin. Microbiol. 36, 2645-2651.

Chen, et al., 1994. Identification of the antigenic constituents of *Ehrlichia chaffeensis*. Am. J. Trop. Med. Hyg. 50, 52-58.

Chen, et al., 1997. Genetic and antigenic diversity of *Ehrlichia chaffeensis*: comparative analysis of a novel human strain from Oklahoma and previously isolated strains. J. Infect. Dis. 175, 856-863.

Dawson, et al., 1992. Susceptibility of dogs to infection with *Ehrlichia chaffeensis*, causative agent of human ehrlichiosis. Am. J. Vet. Res. 53, 1322-1327.

Dawson, et al., 1994. Susceptibility of white-tailed deer (*Odocoileus virginianus*) to infection with *Ehrlichia chaffeensis*, the etiologic agent of human ehrlichiosis. J. Clin. Microbiol. 32, 2725-2728.

Dumler, J. S., Bakken, J. S., 1995. Human granulocytic ehrlichiosis in Wisconsin and Minnesota: A frequent infection with the potential for persistence. J. Infect. Dis. 173, 1027-1030.

Dumler, J. S., Sutker, W, L., Walker, D. H., 1993. Persistent infection with *Ehrlichia chaffeensis*. Clin. Infect. Dis. 17, 903-905.

Eid, et al., 1996. Expression of major surface protein 2 antigenic variants during acute *Anaplasma marginale* rickettsemia. Infect. Immun. 64, 836-841.

Haas, et al., 1986. The repertoire of silent pilus genes in *Neisseria gonorrhoeae*: evidence for gene conversion. Cell 44, 107-115.

Harrus, et al., 1998. Amplification of ehrlichial DNA from dogs 34 months after infection with *Ehrlichia canis*. J. Clin. Microbiol. 36, 73-76.

Horowitz, et al., 1998. Saddleback fever due to human granulocytic ehrlichiosis. Lancet 351, 9103.

French, et al., 1999. Emergence of *Anaplasma marginale* antigenic variants during persistent rickettsemia. Infect. Immun. 67, 5834-5840.

Ijdo, et al., 1998. Cloning of the gene encoding the 44-kilodalton antigen of the agent of human granulocytic ehrlichiosis and characterization of the humoral response. Infect. Immun. 66, 3264-3269.

Klein, et al., 1985. The detection and classification of membrane-spanning proteins. Biochim. Biophys. Acta. 815, 468-476.

McBride, et al., 1999a. Molecular characterization of a new 28-kilodalton protein gene and a multigene locus encoding five homologous 28-kilodalton immunodominant outer membrane proteins of *Ehrlichia canis*. In: Raoult, R., Brouqui, P. (Eds.), Rickettsiae and Rickettsial Diseases at the Turn of the Third Millenium. Elsevier, Paris, France, pp 43-47.

McBride, et al., 1999b. Molecular cloning of a conserved major immunoreactive 28-kilodalton protein gene of *Ehrlichia canis*: a potential serodiagnostic antigen. Clin. Diagn. Lab. Immunol. 6, 392-399.

McGeoch, D. J., 1985. On the predictive recognition of signal peptide sequences. Virus Research 3, 271-286.

Murphy, et al., 1998. Major antigenic proteins of the agent of human granulocytic ehrlichiosis are encoded by members of a multigene family. Infect. Immun. 66, 3711-3718.

Oberle, et al., 1993. Derivation of the complete msp 4 gene sequence of *Anaplasma marginale* without molecular cloning. Gene 136, 291-294.

Ohashi, et al., 1998a. Cloning and characterization of multigenes encoding the immunodominant 30-kilodalton major outer membrane proteins of *Ehrlichia canis* and application of the recombinant protein for serodiagnosis. J. Clin. Microbiol. 36, 2671-2680.

Ohashi, et al., 1998b. Immunodominant major outer membrane proteins of *Ehrlichia chaffeensis* are encoded by a polymorphic multigene family. Infect. Immun. 66, 132-139.

Palmer, et al., 1998. Persistence of *Anaplasma ovis* infection and conservation of the msp-2 and msp-3 multigene families within the genus *Anaplasma*. Infect. Immun. 66, 6035-6039.

Palmer, et al., 1994. The immunoprotective *Anaplasma marginale* major surface protein 2 is encoded by a polymorphic multigene family. Infect. Immun. 62, 3808-3816.

Reddy, et al., 1998. Molecular characterization of a 28 kDa surface antigen gene family of the tribe Ehrlichieae. Biochem. Biophys. Res. Commun. 247, 636-643.

Reddy, G. R., Streck, C. P., 1999. Variability in the 28-kDa surface antigen protein multigene locus of isolates of the emerging disease agent *Ehrlichia chaffeensis* suggests that it plays a role in immune evasion. Mol. Cell Biol. Res. Commun. 1, 167-175.

Rikihisa Y., 1991. The tribe *Ehrlichieae* and ehrlichial diseases. Clin. Microbiol. Rev. 4, 286-308.

Roland, et al., 1995. Ehrlichiosis—A cause of prolonged fever. Clin. Infect. Dis. 20, 821-825.

Schwan, et al., 1998. Bloodstream-versus tick-associated variants of relapsing fever bacterium. Science 280, 1938-1940.

Sulsona, et al., 1999. The map1 gene of *Cowdria ruminantium* is a member of a multigene family containing both conserved and variable genes. Biochem. Biophys. Res. Commun. 257, 300-305.

Swift, B. L., Thomas, G. M., 1983. Bovine anaplasmosis: elimination of the carrier state with injectable long-acting oxytetracycline. JAMA 183, 63-65.

Telford, et al., 1996. Perpetuation of the agent of human granulocytic ehrlichiosis in a deer tick-rodent cycle. Proc. Natl. Acad. Sci. USA 93, 6209-6214.

Von Heijne G., 1986. A new method for predicting signal sequence cleavage sites. Nucl. Acids Res. 14, 4683-4690.

van Vliet, et al., 1994. Molecular cloning, sequencing analysis, and expression of the gene encoding the immunodominant 32-kilodalton protein of *Cowdria ruminantium*. Infect. Immun. 62, 1451-1456.

Weiss, et al., 1989. Energy metabolism of monocytic *Ehrlichia*. Proc. Natl Acad. Sci. USA. 86, 1674-1678.

Yu, X. J., Brouqui, P., Dumler, J. S., Raoult, D., 1993. Detection of *Ehrlichia chaffeensis* in human tissue by using a species-specific monoclonal antibody. J. Clin. Microbiol. 31, 3284-3288.

Yu, et al., 1999a. Characterization of the genus-common outer membrane proteins in *Ehrlichia*. In: Raoult, R., Brouqui P, (Eds.), Rickettsiae and Rickettsial Diseases at the Turn of the Third Millenium. Elsevier, Pris, France, pp 103-107.

Yu, et al., 1999b. Genetic diversity of the 28-kilodalton outer membrane protein of human isolates of *Ehrlichia chaffeensis*. J. Clin. Microbiol. 37, 1137-1143.

Yu, et al., 1999c. Comparison of *Ehrlichia chaffeensis* recombinant proteins for diagnosis of human monocytotropic ehrlichiosis. J. Clin. Microbiol. 37, 2568-2575.

Zaugg, et al., 1986. Transmission of *Anaplasma marginale* Theiler by males of *Dermacentor andersoni* Stiles fed on an Idaho field-infected, chronic carrier cow. Am. J. Vet. Res. 47, 2269-2271.

Any patents or publications mentioned in this specification are indicative of the levels of those skilled in the art to which the invention pertains. These patents and publications are herein incorporated by reference to the same extent as if each individual publication was individually incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated DNA of *E. chaffeensis*, comprising a DNA sequence that encodes the amino acid sequence of SEQ ID NO. 10.

2. An isolated vector comprising the isolated DNA of claim 1.

3. The vector of claim 2, wherein said vector comprises an origin of replication, a promoter, an enhancer, a terminator, a polyadenylation signal, or phenotypic selection.

4. The vector of claim 2, wherein said vector is a plasmid vector or a viral vector.

5. The vector of claim 4, wherein said viral vector is a retroviral vector, an adenoviral vector, an adeno-associated viral vector, an SV40 viral vector, or a herpes viral vector.

6. An isolated host cell transfected with the vector of claim 2, said vector expressing said DNA.

7. The host cell of claim 6, wherein said cell is selected from the group consisting of bacterial cells, mammalian cells, plant cells and insect cells.

8. The host cell of claim 7, wherein said bacterial cells are *E. coli*.

9. The host cell of claim 6, wherein said host cell is from a prokaryote or a eukaryote.

10. The host cell of claim 9, wherein said prokaryote is *E. coli, S. typhimurium, Serratia marcescens* or *Bacillus subtilis*.

11. The host cell of claim 9, wherein said eukaryote is a yeast, an animal, or a plant.

12. The host cell of claim 11, wherein the animal is a mammal or an insect.

* * * * *

SEQUENCE LISTING

```
<160> NUMBER OF SEQ ID NOS: 53

<210> SEQ ID NO 1
<211> LENGTH: 284
<212> TYPE: PRT
<213> ORGANISM: Ehrlichia chaffeensis
<220> FEATURE:
<223> OTHER INFORMATION: P28-1 Outer Membrane Protein of
      Ehrlichia chaffeensis

<400> SEQUENCE: 1

Met Ser Lys Arg Ser Asn Arg Lys Phe Val Leu Trp Val Met Leu
              5                   10                  15

Ile Leu Phe Thr Pro His Ile Ser Leu Ala Ser Val Leu Asn Asp
             20                  25                  30
```

His Asn Ser Met Tyr Val Gly Ile Gln Tyr Lys Pro Ala Arg Gln
                35                  40                  45

His Leu Ser Lys Leu Leu Ile Lys Glu Ser Ala Ala Asn Thr Val
                50                  55                  60

Glu Val Phe Gly Leu Lys Lys Asp Leu Leu Asn Asp Leu Leu Thr
                65                  70                  75

Gly Ile Lys Asp Asn Thr Asn Phe Asn Ile Lys Tyr Asn Pro Tyr
                80                  85                  90

Tyr Glu Asn Asn Arg Leu Gly Phe Ser Gly Ile Phe Gly Tyr Tyr
                95                 100                 105

Tyr Asn Lys Asn Phe Arg Ile Glu Ser Glu Leu Ser Tyr Glu Thr
               110                 115                 120

Phe His Ile Lys Asn Asn Gly Tyr Lys Arg Ile Asp Cys Glu Lys
               125                 130                 135

His Phe Ala Leu Ala Lys Glu Ile Ser Gly Gly Ser Asn Asn Pro
               140                 145                 150

Ala Asn Asn Lys Tyr Val Thr Leu Ile Asn Asn Gly Ile Ser Leu
               155                 160                 165

Thr Ser Ala Leu Ile Asn Val Cys Tyr Asp Val Asp Gly Leu Lys
               170                 175                 180

His Asn Ile Ile Thr Tyr Ser Cys Leu Gly Phe Gly Val Asp Thr
               185                 190                 195

Ile Asp Phe Leu Ser Lys Tyr Thr Thr Lys Phe Ser Tyr Gln Gly
               200                 205                 210

Lys Leu Gly Ala Ser Tyr Thr Val Ser Pro Gln Val Ser Val Phe
               215                 220                 225

Ile Glu Gly Tyr Tyr His Gly Leu Phe Gly Lys Lys Phe Glu Lys
               230                 235                 240

Ile Pro Val Asn Tyr Pro Cys Asp Tyr Pro Ser Pro Thr Pro Pro
               245                 250                 255

Asn Ser Lys Pro His Val His Thr Thr Ala Leu Ala Met Leu Ser
               260                 265                 270

Ile Gly Tyr Tyr Gly Gly Ser Ile Gly Ile Lys Phe Ile Leu
               275                 280

<210> SEQ ID NO 2
<211> LENGTH: 297
<212> TYPE: PRT
<213> ORGANISM: Ehrlichia chaffeensis
<220> FEATURE:
<223> OTHER INFORMATION: P28-2 Outer Membrane Protein of
      Ehrlichia chaffeensis

<400> SEQUENCE: 2

Met Ser Tyr Ala Lys Val Phe Ile Leu Ile Cys Leu Ile Leu Leu
                 5                  10                  15

Val Pro Ser Leu Ser Phe Ala Ile Val Asn Asn Asp Phe Leu Lys
                20                  25                  30

Asp Asn Ile Gly His Phe Tyr Ile Gly Gly Gln Tyr Lys Pro Gly
                35                  40                  45

Val Pro Arg Phe Asn Arg Phe Leu Val Thr Asn Asn Asn Ile Arg
                50                  55                  60

Glu Leu Met Ser Ser Asp Glu Glu Cys Arg Ser Thr Ile Pro His
                65                  70                  75

Met Val Gln Ser Val Ala Gln Gly Thr Leu Pro Pro Glu Ala Leu

-continued

```
                    80                  85                  90
Glu Glu Leu Ala Asp Gly Lys Phe Pro Glu Gly Tyr Leu Tyr Phe
                    95                 100                 105
Thr Ile Pro Tyr Asn Pro Thr Tyr Lys Lys Asn Leu Leu Gly Ala
                   110                 115                 120
Gly Gly Val Ile Gly Tyr Ser Thr Thr His Phe Arg Val Glu Val
                   125                 130                 135
Glu Ala Phe Tyr Asp Lys Phe Asn Leu Thr Ala Pro Ala Gly Tyr
                   140                 145                 150
Leu His Lys Asn Phe Tyr Glu Tyr Phe Ala Leu Ala Thr Thr Met
                   155                 160                 165
Asp Thr Lys His Pro His Gln Ser Ala Glu Asp Lys Tyr Tyr Tyr
                   170                 175                 180
Met Lys Asn Thr Gly Ile Thr Leu Ser Pro Phe Ile Ile Asn Ala
                   185                 190                 195
Cys Tyr Asp Phe Ile Leu Lys Lys Thr Arg Asn Val Ala Pro Tyr
                   200                 205                 210
Leu Cys Leu Gly Val Gly Gly Asn Phe Ile Asp Phe Leu Asp Gln
                   215                 220                 225
Val Ser Phe Lys Phe Ala Tyr Gln Ala Lys Val Gly Ile Ser Tyr
                   230                 235                 240
Phe Val Ser Pro Asn Ile Ala Phe Phe Ile Asp Gly Ser Phe His
                   245                 250                 255
Gly His Leu Asn Asn Gln Phe Ser Asp Ser Pro Val Val Asp Tyr
                   260                 265                 270
Ser Ser Ser Gly Phe Pro Thr Ile Ser Ala Lys Phe Asn Ala Asn
                   275                 280                 285
Phe Leu Thr Ser Ser Ile Gly Ile Arg Phe Ile Ser
                   290                 295

<210> SEQ ID NO 3
<211> LENGTH: 285
<212> TYPE: PRT
<213> ORGANISM: Ehrlichia chaffeensis
<220> FEATURE:
<223> OTHER INFORMATION: P28-3 Outer Membrane Protein of
      Ehrlichia chaffeensis

<400> SEQUENCE: 3

Met Gln Lys Leu Tyr Ile Ser Phe Ile Ile Leu Ser Gly Leu Leu
                     5                  10                  15
Leu Pro Lys Tyr Val Phe Cys Met His Gln Asn Asn Asn Ile Asp
                    20                  25                  30
Gly Ser Tyr Val Thr Ile Lys Tyr Gln Leu Thr Thr Pro His Phe
                    35                  40                  45
Lys Asn Phe Tyr Ile Lys Glu Thr Asp Phe Asp Thr Gln Glu Pro
                    50                  55                  60
Ile Gly Leu Ala Lys Ile Thr Ala Asn Thr Lys Phe Asp Thr Leu
                    65                  70                  75
Lys Glu Asn Phe Ser Phe Ser Pro Leu His Gln Thr Asp Ser Tyr
                    80                  85                  90
Lys Ser Tyr Gln Asn Asp Leu Leu Gly Ile Gly Leu Ser Val Gly
                    95                 100                 105
Leu Phe Val Lys Ser Phe Arg Ile Glu Phe Glu Gly Ala Tyr Lys
                   110                 115                 120
```

```
Asn Phe Asn Thr Lys Arg Leu Ala Arg Tyr Lys Ser Lys Asp Gly
            125                 130                 135

Tyr Lys Tyr Phe Ala Ile Pro Arg Lys Ser Glu His Gly Phe Leu
            140                 145                 150

Asp Asn Thr Phe Gly Tyr Thr Val Ala Lys Asn Asn Gly Ile Ser
            155                 160                 165

Ile Ile Ser Asn Ile Ile Asn Leu Cys Ser Glu Thr Lys Tyr Lys
            170                 175                 180

Ser Phe Thr Pro Tyr Ile Cys Ile Gly Val Gly Gly Asp Phe Ile
            185                 190                 195

Glu Ile Phe Asp Val Met Arg Ile Lys Phe Ala Tyr Gln Gly Lys
            200                 205                 210

Val Gly Val Ser Tyr Pro Ile Thr Ser Lys Leu Ile Leu Ser Ile
            215                 220                 225

Asn Gly Gln Tyr His Lys Val Ile Gly Asn Lys Phe Glu Leu Leu
            230                 235                 240

Pro Val Tyr Gln Pro Val Glu Leu Lys Arg Leu Val Thr Asn Lys
            245                 250                 255

Thr Ser Lys Asp Ile Asp Gln Asp Val Thr Ala Ser Leu Thr Leu
            260                 265                 270

Asn Leu Glu His Phe Ser Ser Glu Ile Gly Leu Ser Phe Ile Phe
            275                 280                 285

<210> SEQ ID NO 4
<211> LENGTH: 272
<212> TYPE: PRT
<213> ORGANISM: Ehrlichia chaffeensis
<220> FEATURE:
<223> OTHER INFORMATION: P28-4 Outer Membrane Protein of
      Ehrlichia chaffeensis

<400> SEQUENCE: 4

Met Tyr Met Tyr Asn Lys Lys His Tyr Cys Tyr Ile Val Thr Tyr
              5                  10                   15

Val Ile Thr Leu Phe Phe Leu Leu Pro Ile Glu Ser Leu Ser
             20                  25                   30

Ala Leu Ile Gly Asn Val Glu Lys Asp Leu Lys Val Ser Ser Thr
             35                  40                   45

Tyr Val Ser Ser Gln Tyr Lys Pro Ser Ile Phe His Phe Arg Asn
             50                  55                   60

Phe Ser Ile Gln Glu Ser His Pro Lys Lys Ser Ser Glu Glu Phe
             65                  70                   75

Lys Lys Ile Lys Ala Asn Leu Asn Asn Ile Leu Lys Ser Asn Ala
             80                  85                   90

Tyr Asn Leu Gln Phe Gln Asp Asn Thr Thr Ser Phe Ser Gly Thr
             95                 100                  105

Ile Gly Tyr Phe Ser Lys Gly Leu Arg Leu Glu Ala Glu Gly Cys
            110                 115                  120

Tyr Gln Glu Phe Asn Val Lys Asn Ser Asn Ser Leu Ile Ile
            125                 130                  135

Ser Ser Asn Lys Tyr His Ser Arg Ile His Asp Glu Asn Tyr Ala
            140                 145                  150

Ile Thr Thr Asn Asn Lys Leu Ser Ile Ala Ser Ile Met Val Asn
            155                 160                  165

Thr Cys Tyr Asp Ile Ser Ile Asn Asn Thr Ser Ile Val Pro Tyr
            170                 175                  180
```

```
Leu Cys Thr Gly Ile Gly Glu Asp Leu Val Gly Leu Phe Asn Thr
                185                 190                 195

Ile His Phe Lys Leu Ala Tyr Gln Gly Lys Val Gly Met Ser Tyr
                200                 205                 210

Leu Ile Asn Asn Asn Ile Leu Leu Phe Ser Asp Ile Tyr Tyr His
                215                 220                 225

Lys Val Met Gly Asn Arg Phe Lys Asn Leu Tyr Met Gln Tyr Val
                230                 235                 240

Ala Asp Pro Asn Ile Ser Glu Glu Thr Ile Pro Ile Leu Ala Lys
                245                 250                 255

Leu Asp Ile Gly Tyr Phe Gly Ser Glu Ile Gly Ile Arg Phe Met
                260                 265                 270

Phe Asn

<210> SEQ ID NO 5
<211> LENGTH: 295
<212> TYPE: PRT
<213> ORGANISM: Ehrlichia chaffeensis
<220> FEATURE:
<223> OTHER INFORMATION: P28-5 Outer Membrane Protein of
      Ehrlichia chaffeensis

<400> SEQUENCE: 5

Met Thr Lys Lys Phe Asn Phe Val Asn Val Ile Leu Thr Phe Leu
                 5                  10                  15

Leu Phe Leu Phe Pro Leu Lys Ser Phe Thr Thr Tyr Ala Asn Asn
                20                  25                  30

Asn Thr Ile Thr Gln Lys Val Gly Leu Tyr Ile Ser Gly Gln Tyr
                35                  40                  45

Lys Pro Ser Ile Pro His Phe Lys Asn Phe Ser Val Glu Glu Asn
                50                  55                  60

Asp Lys Val Val Asp Leu Ile Gly Leu Thr Thr Asp Val Thr Tyr
                65                  70                  75

Ile Thr Glu His Ile Leu Arg Asp Asn Thr Lys Phe Asn Thr His
                80                  85                  90

Tyr Ile Ala Lys Phe Lys Asn Asn Phe Ile Asn Phe Ser Ser Ala
                95                 100                 105

Ile Gly Tyr Tyr Ser Gly Gln Gly Pro Arg Leu Glu Ile Glu Ser
                110                 115                 120

Ser Tyr Gly Asp Phe Asp Val Val Asn Tyr Lys Asn Tyr Ala Val
                125                 130                 135

Gln Asp Val Asn Arg Tyr Phe Ala Leu Val Arg Glu Lys Asn Gly
                140                 145                 150

Ser Asn Phe Ser Pro Lys Pro His Glu Thr Ser Gln Pro Ser Asp
                155                 160                 165

Ser Asn Pro Lys Lys Ser Phe Tyr Thr Leu Met Lys Asn Asn Gly
                170                 175                 180

Val Phe Val Ala Ser Val Ile Ile Asn Gly Cys Tyr Asp Phe Ser
                185                 190                 195

Phe Asn Asn Thr Thr Ile Ser Pro Tyr Val Cys Ile Gly Val Gly
                200                 205                 210

Gly Asp Phe Ile Glu Phe Phe Glu Val Met His Ile Lys Phe Ala
                215                 220                 225

Cys Gln Ser Lys Val Gly Ile Ser Tyr Pro Ile Ser Pro Ser Ile
                230                 235                 240
```

```
Thr Ile Phe Ala Asp Ala His Tyr His Lys Val Ile Asn Asn Lys
            245                 250                 255

Phe Asn Asn Leu His Val Lys Tyr Ser Tyr Glu Leu Lys Asn Ser
            260                 265                 270

Pro Thr Ile Thr Ser Ala Thr Ala Lys Leu Asn Ile Glu Tyr Phe
            275                 280                 285

Gly Gly Glu Val Gly Met Arg Phe Ile Phe
            290                 295

<210> SEQ ID NO 6
<211> LENGTH: 279
<212> TYPE: PRT
<213> ORGANISM: Ehrlichia chaffeensis
<220> FEATURE:
<223> OTHER INFORMATION: P28-6 Outer Membrane Protein of
      Ehrlichia chaffeensis

<400> SEQUENCE: 6

Met Ser Lys Lys Lys Phe Ile Thr Ile Gly Thr Val Leu Ala Ser
              5                  10                  15

Leu Leu Ser Phe Leu Ser Ile Glu Ser Phe Ser Ala Ile Asn His
             20                  25                  30

Asn His Thr Gly Asn Asn Thr Ser Gly Ile Tyr Ile Thr Gly Gln
             35                  40                  45

Tyr Arg Pro Gly Val Ser His Phe Ser Asn Phe Ser Val Lys Glu
             50                  55                  60

Thr Asn Val Asp Thr Ile Gln Leu Val Gly Tyr Lys Lys Ser Ala
             65                  70                  75

Ser Ser Ile Asp Pro Asn Thr Tyr Ser Asn Phe Gln Gly Pro Tyr
             80                  85                  90

Thr Val Thr Phe Gln Asp Asn Ala Ala Ser Phe Ser Gly Ala Ile
             95                 100                 105

Gly Tyr Ser Tyr Pro Glu Ser Leu Arg Leu Glu Leu Glu Gly Ser
            110                 115                 120

Tyr Glu Lys Phe Asp Val Lys Asp Pro Lys Asp Tyr Ser Ala Lys
            125                 130                 135

Asp Ala Phe Arg Phe Phe Ala Leu Ala Arg Asn Thr Ser Thr Thr
            140                 145                 150

Val Pro Asp Ala Gln Lys Tyr Thr Val Met Lys Asn Asn Gly Leu
            155                 160                 165

Ser Val Ala Ser Ile Met Ile Asn Gly Cys Tyr Asp Leu Ser Phe
            170                 175                 180

Asn Asn Leu Val Val Ser Pro Tyr Ile Cys Ala Gly Ile Gly Glu
            185                 190                 195

Asp Phe Ile Glu Phe Phe Asp Thr Leu His Ile Lys Leu Ala Tyr
            200                 205                 210

Gln Gly Lys Leu Gly Ile Ser Tyr Tyr Phe Pro Lys Ile Asn
            215                 220                 225

Val Phe Ala Gly Gly Tyr Tyr His Arg Val Ile Gly Asn Lys Phe
            230                 235                 240

Lys Asn Leu Asn Val Asn His Val Val Thr Pro Asp Glu Phe Pro
            245                 250                 255

Lys Ala Thr Ser Ala Val Ala Thr Leu Asn Val Ala Tyr Phe Gly
            260                 265                 270

Gly Glu Ala Gly Val Lys Phe Thr Phe
```

-continued

```
                275

<210> SEQ ID NO 7
<211> LENGTH: 283
<212> TYPE: PRT
<213> ORGANISM: Ehrlichia chaffeensis
<220> FEATURE:
<223> OTHER INFORMATION: P28-7 Outer Membrane Protein of
      Ehrlichia chaffeensis

<400> SEQUENCE: 7

Met Ser Ala Lys Lys Lys Leu Phe Ile Ile Gly Ser Val Leu Val
                5                   10                  15

Cys Leu Val Ser Tyr Leu Pro Thr Lys Ser Leu Ser Asn Leu Asn
                20                  25                  30

Asn Ile Asn Asn Asn Thr Lys Cys Thr Gly Leu Tyr Val Ser Gly
                35                  40                  45

Gln Tyr Lys Pro Thr Val Ser His Phe Ser Asn Phe Ser Leu Lys
                50                  55                  60

Glu Thr Tyr Thr Asp Thr Lys Glu Leu Leu Gly Leu Ala Lys Asp
                65                  70                  75

Ile Lys Ser Ile Thr Asp Ile Thr Thr Asn Lys Lys Phe Asn Ile
                80                  85                  90

Pro Tyr Asn Thr Lys Phe Gln Asp Asn Ala Val Ser Phe Ser Ala
                95                  100                 105

Ala Val Gly Tyr Ile Ser Gln Asp Ser Pro Arg Val Glu Val Glu
                110                 115                 120

Trp Ser Tyr Glu Glu Phe Asp Val Lys Asn Pro Gly Asn Tyr Val
                125                 130                 135

Val Ser Glu Ala Phe Arg Tyr Ile Ala Leu Ala Arg Gly Ile Asp
                140                 145                 150

Asn Leu Gln Lys Tyr Pro Glu Thr Asn Lys Tyr Val Val Ile Lys
                155                 160                 165

Asn Asn Gly Leu Ser Val Ala Ser Ile Ile Ile Asn Gly Cys Tyr
                170                 175                 180

Asp Phe Ser Leu Asn Asn Leu Lys Val Ser Pro Tyr Ile Cys Val
                185                 190                 195

Gly Phe Gly Gly Asp Ile Ile Glu Phe Phe Ser Ala Val Ser Phe
                200                 205                 210

Lys Phe Ala Tyr Gln Gly Lys Val Gly Ile Ser Tyr Pro Leu Phe
                215                 220                 225

Ser Asn Met Ile Ile Phe Ala Asp Gly Tyr Tyr His Lys Val Ile
                230                 235                 240

Gly Asn Lys Phe Asn Asn Leu Asn Val Gln His Val Val Ser Leu
                245                 250                 255

Asn Ser His Pro Lys Ser Thr Phe Ala Val Ala Thr Leu Asn Val
                260                 265                 270

Glu Tyr Phe Gly Ser Glu Phe Gly Leu Lys Phe Ile Phe
                275                 280

<210> SEQ ID NO 8
<211> LENGTH: 275
<212> TYPE: PRT
<213> ORGANISM: Ehrlichia chaffeensis
<220> FEATURE:
<223> OTHER INFORMATION: P28-8 Outer Membrane Protein of
      Ehrlichia chaffeensis
```

<400> SEQUENCE: 8

Met Ser Lys Lys Asn Phe Ile Thr Ile Gly Ala Thr Leu Ile His
 1               5                  10                  15

Met Leu Leu Pro Asn Ile Ser Phe Pro Glu Thr Ile Asn Asn Asn
             20                  25                  30

Thr Asp Lys Leu Ser Gly Leu Tyr Ile Ser Gly Gln Tyr Lys Pro
         35                  40                  45

Gly Ile Ser His Phe Ser Lys Phe Ser Val Lys Glu Ile Tyr Asn
     50                  55                  60

Asp Asn Ile Gln Leu Ile Gly Leu Arg His Asn Ala Ile Ser Thr
 65                  70                  75

Ser Thr Leu Asn Ile Asn Thr Asp Phe Asn Ile Pro Tyr Lys Val
             80                  85                  90

Thr Phe Gln Asn Asn Ile Thr Ser Phe Ser Gly Ala Ile Gly Tyr
         95                 100                 105

Ser Asp Pro Thr Gly Ala Arg Phe Glu Leu Glu Gly Ser Tyr Glu
    110                 115                 120

Glu Phe Asp Val Thr Asp Pro Gly Asp Cys Leu Ile Lys Asp Thr
125                 130                 135

Tyr Arg Tyr Phe Ala Leu Ala Arg Asn Pro Ser Gly Ser Ser Pro
            140                 145                 150

Thr Ser Asn Asn Tyr Thr Val Met Arg Asn Asp Gly Val Ser Ile
        155                 160                 165

Thr Ser Val Ile Phe Asn Gly Cys Tyr Asp Ile Phe Leu Lys Asp
    170                 175                 180

Leu Glu Val Ser Pro Tyr Val Cys Val Gly Val Gly Gly Asp Phe
185                 190                 195

Ile Glu Phe Phe Asp Ala Leu His Ile Lys Leu Ala Tyr Gln Gly
            200                 205                 210

Lys Leu Gly Ile Asn Tyr His Leu Ser Thr Gln Ala Ser Val Phe
        215                 220                 225

Ile Asp Gly Tyr Tyr His Lys Val Ile Gly Asn Gln Phe Asn Asn
    230                 235                 240

Leu Asn Val Gln His Val Ala Ser Thr Asp Phe Gly Pro Val Tyr
245                 250                 255

Ala Val Ala Thr Leu Asn Ile Gly Tyr Phe Gly Gly Glu Ile Gly
            260                 265                 270

Ile Arg Leu Thr Phe
        275

<210> SEQ ID NO 9
<211> LENGTH: 285
<212> TYPE: PRT
<213> ORGANISM: Ehrlichia chaffeensis
<220> FEATURE:
<223> OTHER INFORMATION: P28-9 Outer Membrane Protein of
      Ehrlichia chaffeensis

<400> SEQUENCE: 9

Met Asn Asn Arg Lys Ser Phe Phe Ile Ile Gly Ala Ser Leu Leu
 1               5                  10                  15

Ala Ser Leu Leu Phe Thr Ser Glu Ala Ser Ser Thr Gly Asn Val
             20                  25                  30

Ser Asn His Thr Tyr Phe Lys Pro Arg Leu Tyr Ile Ser Gly Gln
         35                  40                  45

-continued

Tyr Arg Pro Gly Val Ser His Phe Ser Lys Phe Ser Val Lys Glu
                    50                  55                  60

Thr Asn Tyr Asn Thr Thr Gln Leu Val Gly Leu Lys Lys Asp Ile
                65                  70                  75

Ser Val Ile Gly Asn Ser Asn Ile Thr Thr Tyr Thr Asn Phe Asn
            80                  85                  90

Phe Pro Tyr Ile Ala Glu Phe Gln Asp Asn Ala Ile Ser Phe Ser
        95                  100                 105

Gly Ala Ile Gly Tyr Leu Tyr Ser Glu Asn Phe Arg Ile Glu Val
            110                 115                 120

Glu Ala Ser Tyr Glu Glu Phe Asp Val Lys Asn Pro Glu Gly Ser
            125                 130                 135

Ala Thr Asp Ala Tyr Arg Tyr Phe Ala Leu Ala Arg Ala Met Asp
            140                 145                 150

Gly Thr Asn Lys Ser Ser Pro Asp Asp Thr Arg Lys Phe Thr Val
            155                 160                 165

Met Arg Asn Asp Gly Leu Ser Ile Ser Ser Val Met Ile Asn Gly
            170                 175                 180

Cys Tyr Asn Phe Thr Leu Asp Asp Ile Pro Val Val Pro Tyr Val
            185                 190                 195

Cys Ala Gly Ile Gly Gly Asp Phe Ile Glu Phe Phe Asn Asp Leu
            200                 205                 210

His Val Lys Phe Ala His Gln Gly Lys Val Gly Ile Ser Tyr Ser
            215                 220                 225

Ile Ser Pro Glu Val Ser Leu Phe Leu Asn Gly Tyr Tyr His Lys
            230                 235                 240

Val Thr Gly Asn Arg Phe Lys Asn Leu His Val Gln His Val Ser
            245                 250                 255

Asp Leu Ser Asp Ala Pro Lys Phe Thr Ser Ala Val Ala Thr Leu
            260                 265                 270

Asn Val Gly Tyr Phe Gly Gly Glu Ile Gly Val Arg Phe Ile Phe
            275                 280                 285

<210> SEQ ID NO 10
<211> LENGTH: 291
<212> TYPE: PRT
<213> ORGANISM: Ehrlichia chaffeensis
<220> FEATURE:
<223> OTHER INFORMATION: P28-10 Outer Membrane Protein of
      Ehrlichia chaffeensis

<400> SEQUENCE: 10

Met Asn Lys Lys Asn Lys Phe Ile Ile Ala Thr Ala Leu Val Tyr
                    5                   10                  15

Leu Leu Ser Leu Pro Ser Val Ser Phe Ser Glu Val Thr Asn Ser
                20                  25                  30

Ser Ile Lys Lys His Ser Gly Leu Tyr Ile Ser Gly Gln Tyr Lys
                35                  40                  45

Pro Ser Val Ser Val Phe Ser Ser Phe Ser Ile Lys Glu Thr Asn
                50                  55                  60

Thr Ile Thr Lys Ile Leu Ile Ala Leu Lys Lys Asp Ile Asn Ser
                65                  70                  75

Leu Glu Val Asn Ala Asp Ala Ser Gln Gly Ile Ser His Pro Gly
                80                  85                  90

Asn Phe Thr Ile Pro Tyr Ile Ala Ala Phe Glu Asp Asn Ala Phe
                95                  100                 105

```
Asn Phe Asn Gly Ala Ile Gly Tyr Ile Thr Glu Gly Leu Arg Ile
            110                 115                 120

Glu Ile Glu Gly Ser Tyr Glu Phe Asp Ala Lys Asn Pro Gly
        125                 130                 135

Gly Tyr Gly Leu Asn Asp Ala Phe Arg Tyr Phe Ala Leu Ala Arg
            140                 145                 150

Asp Met Glu Ser Asn Lys Phe Gln Pro Lys Ala Gln Ser Ser Gln
            155                 160                 165

Lys Val Phe His Thr Val Met Lys Ser Asp Gly Leu Ser Ile Ile
            170                 175                 180

Ser Ile Met Gly Asn Gly Trp Tyr Asp Phe Ser Ser Asp Asn Leu
            185                 190                 195

Leu Val Ser Pro Tyr Ile Cys Gly Gly Ile Gly Val Asp Ala Ile
            200                 205                 210

Glu Phe Phe Asp Ala Leu His Ile Lys Leu Ala Cys Pro Ser Lys
            215                 220                 225

Leu Gly Ile Thr Tyr Gln Leu Ser Tyr Asn Ile Ser Leu Phe Ala
            230                 235                 240

Val Gly Phe Tyr His Gln Val Ile Gly Asn Gln Phe Arg Asn Leu
            245                 250                 255

Asn Val Gln His Val Ala Glu Leu Asn Asp Ala Pro Lys Val Thr
            260                 265                 270

Ser Ala Val Ala Thr Leu Asn Val Gly Tyr Phe Gly Ala Glu Val
            275                 280                 285

Gly Val Arg Phe Ile Phe
            290

<210> SEQ ID NO 11
<211> LENGTH: 298
<212> TYPE: PRT
<213> ORGANISM: Ehrlichia chaffeensis
<220> FEATURE:
<223> OTHER INFORMATION: P28-11 Outer Membrane Protein of
      Ehrlichia chaffeensis

<400> SEQUENCE: 11

Met Asn His Lys Ser Met Leu Phe Thr Ile Gly Thr Ala Leu Ile
              5                  10                  15

Ser Leu Leu Ser Leu Pro Asn Val Ser Phe Ser Gly Ile Ile Asn
             20                  25                  30

Asn Asn Ala Asn Asn Leu Gly Ile Tyr Ile Ser Gly Gln Tyr Lys
             35                  40                  45

Pro Ser Val Ser Val Phe Ser Asn Phe Ser Val Lys Glu Thr Asn
             50                  55                  60

Phe Thr Thr Gln Gln Leu Val Ala Leu Lys Lys Asp Ile Asp Ser
             65                  70                  75

Val Asp Ile Ser Thr Asn Ala Asp Ser Gly Ile Asn Asn Pro Gln
             80                  85                  90

Asn Phe Thr Ile Pro Tyr Ile Pro Lys Phe Gln Asp Asn Ala Ala
             95                 100                 105

Ser Phe Ser Gly Ala Leu Gly Phe Phe Tyr Ala Arg Gly Leu Arg
            110                 115                 120

Leu Glu Met Glu Gly Ser Tyr Glu Glu Phe Asp Val Lys Asn Pro
            125                 130                 135

Gly Gly Tyr Thr Lys Val Lys Asp Ala Tyr Arg Tyr Phe Ala Leu
```

-continued

```
                140                 145                 150
Ala Arg Glu Met Gln Ser Gly Gln Thr Cys Pro Lys His Lys Glu
            155                 160                 165
Thr Ser Gly Ile Gln Pro His Gly Ile Tyr His Thr Val Met Arg
            170                 175                 180
Asn Asp Gly Val Ser Ile Ser Ser Val Ile Ile Asn Gly Cys Tyr
            185                 190                 195
Asn Phe Thr Leu Ser Asn Leu Pro Ile Ser Pro Tyr Met Cys Val
            200                 205                 210
Gly Met Gly Ile Asp Ala Ile Gln Phe Phe Asp Ser Leu His Ile
            215                 220                 225
Lys Phe Ala His Gln Ser Lys Leu Gly Ile Thr Tyr Pro Leu Ser
            230                 235                 240
Ser Asn Val His Leu Phe Ala Asp Ser Tyr Tyr His Lys Val Ile
            245                 250                 255
Gly Asn Lys Phe Lys Asn Leu Arg Val Gln His Val Tyr Glu Leu
            260                 265                 270
Gln Gln Val Pro Lys Val Thr Ser Ala Val Ala Thr Leu Asp Ile
            275                 280                 285
Gly Tyr Phe Gly Gly Glu Val Gly Val Arg Phe Ile Leu
            290                 295

<210> SEQ ID NO 12
<211> LENGTH: 300
<212> TYPE: PRT
<213> ORGANISM: Ehrlichia chaffeensis
<220> FEATURE:
<223> OTHER INFORMATION: P28-12 Outer Membrane Protein of
      Ehrlichia chaffeensis

<400> SEQUENCE: 12

Met Lys Lys Lys Asn Gln Phe Ile Thr Ile Ser Thr Ile Leu Val
              5                  10                  15
Cys Leu Leu Ser Leu Ser Asn Ala Ser Leu Ser Asn Thr Thr Asn
             20                  25                  30
Ser Ser Thr Lys Lys Gln Phe Gly Leu Tyr Val Ser Gly Gln Tyr
             35                  40                  45
Lys Pro Ser Val Ser Ile Phe Ser Asn Phe Ser Val Lys Glu Thr
             50                  55                  60
Asn Phe Pro Thr Lys Tyr Leu Ala Ala Leu Lys Lys Asp Ile Asn
             65                  70                  75
Ser Val Glu Phe Asp Asp Ser Val Thr Ala Gly Ile Ser Tyr Pro
             80                  85                  90
Leu Asn Phe Ser Thr Pro Tyr Ile Ala Val Phe Gln Asp Asn Ile
             95                 100                 105
Ser Asn Phe Asn Gly Ala Ile Gly Tyr Thr Phe Val Glu Gly Pro
            110                 115                 120
Arg Ile Glu Ile Glu Gly Ser Tyr Glu Glu Phe Asp Val Lys Asp
            125                 130                 135
Pro Gly Arg Tyr Thr Glu Ile Gln Asp Ala Tyr Arg Tyr Phe Ala
            140                 145                 150
Leu Ala Arg Asp Ile Asp Ser Ile Pro Thr Ser Pro Lys Asn Arg
            155                 160                 165
Thr Ser His Asp Gly Asn Ser Ser Tyr Lys Val Tyr His Thr Val
            170                 175                 180
```

```
Met Lys Asn Glu Gly Leu Ser Ile Ile Ser Ile Met Val Asn Gly
            185                 190                 195

Cys Tyr Asp Phe Ser Ser Asp Asn Leu Ser Ile Leu Pro Tyr Val
            200                 205                 210

Cys Gly Gly Ile Gly Val Asn Ala Ile Glu Phe Phe Asp Ala Leu
            215                 220                 225

His Val Lys Phe Ala Cys Gln Gly Lys Leu Gly Ile Thr Tyr Pro
            230                 235                 240

Leu Ser Ser Asn Val Ser Leu Phe Ala Gly Gly Tyr Tyr His Gln
            245                 250                 255

Val Met Gly Asn Gln Phe Lys Asn Leu Asn Val Gln His Val Ala
            260                 265                 270

Glu Leu Asn Asp Ala Pro Lys Val Thr Ser Ala Val Ala Thr Leu
            275                 280                 285

Asp Ile Gly Tyr Phe Gly Gly Glu Ile Gly Ala Arg Leu Ile Phe
            290                 295                 300
```

<210> SEQ ID NO 13
<211> LENGTH: 293
<212> TYPE: PRT
<213> ORGANISM: Ehrlichia chaffeensis
<220> FEATURE:
<223> OTHER INFORMATION: P28-13 Outer Membrane Protein of
      Ehrlichia chaffeensis

<400> SEQUENCE: 13

```
Met Asn Lys Lys Asn Lys Phe Phe Thr Ile Ser Thr Ala Met Val
              5                  10                  15

Cys Leu Leu Leu Leu Pro Gly Ile Ser Phe Ser Glu Thr Ile Asn
             20                  25                  30

Asn Ser Ala Lys Lys Gln Pro Gly Leu Tyr Ile Ser Gly Gln Tyr
             35                  40                  45

Lys Pro Ser Val Ser Val Phe Ser Asn Phe Ser Val Lys Glu Thr
             50                  55                  60

Asn Val Pro Thr Lys Gln Leu Ile Ala Leu Lys Lys Asp Ile Asn
             65                  70                  75

Ser Val Ala Val Gly Ser Asn Ala Thr Thr Gly Ile Ser Asn Pro
             80                  85                  90

Gly Asn Phe Thr Ile Pro Tyr Thr Ala Glu Phe Gln Asp Asn Val
             95                 100                 105

Ala Asn Phe Asn Gly Ala Val Gly Tyr Ser Phe Pro Asp Ser Leu
            110                 115                 120

Arg Ile Glu Ile Glu Gly Phe His Glu Lys Phe Asp Val Lys Asn
            125                 130                 135

Pro Gly Gly Tyr Thr Gln Val Lys Asp Ala Tyr Arg Tyr Phe Ala
            140                 145                 150

Leu Ala Arg Asp Leu Lys Asp Gly Phe Phe Glu Pro Lys Ala Glu
            155                 160                 165

Asp Thr Gly Val Tyr His Thr Val Met Lys Asn Asp Gly Leu Ser
            170                 175                 180

Ile Leu Ser Thr Met Val Asn Val Cys Tyr Asp Phe Ser Val Asp
            185                 190                 195

Glu Leu Pro Val Leu Pro Tyr Ile Cys Ala Gly Met Gly Ile Asn
            200                 205                 210

Ala Ile Glu Phe Phe Asp Ala Leu His Val Lys Phe Ala Tyr Gln
            215                 220                 225
```

-continued

```
Gly Lys Leu Gly Ile Ser Tyr Gln Leu Phe Thr Lys Val Asn Leu
                230                 235                 240

Phe Leu Asp Gly Tyr Tyr His Gln Val Ile Gly Asn Gln Phe Lys
                245                 250                 255

Asn Leu Asn Val Asn His Val Tyr Thr Leu Lys Glu Ser Pro Lys
                260                 265                 270

Val Thr Ser Ala Val Ala Thr Leu Asp Ile Ala Tyr Phe Gly Gly
                275                 280                 285

Glu Val Gly Ile Arg Phe Thr Phe
                290

<210> SEQ ID NO 14
<211> LENGTH: 283
<212> TYPE: PRT
<213> ORGANISM: Ehrlichia chaffeensis
<220> FEATURE:
<223> OTHER INFORMATION: P28-14 Outer Membrane Protein of
      Ehrlichia chaffeensis

<400> SEQUENCE: 14

Met Asn Tyr Lys Lys Ile Phe Val Ser Ser Ala Leu Ile Ser Leu
                  5                  10                  15

Met Ser Ile Leu Pro Tyr Gln Ser Phe Ala Asp Pro Val Thr Ser
                 20                  25                  30

Asn Asp Thr Gly Ile Asn Asp Ser Arg Glu Gly Phe Tyr Ile Ser
                 35                  40                  45

Val Lys Tyr Asn Pro Ser Ile Ser His Phe Arg Lys Phe Ser Ala
                 50                  55                  60

Glu Glu Ala Pro Ile Asn Gly Asn Thr Ser Ile Thr Lys Lys Val
                 65                  70                  75

Phe Gly Leu Lys Lys Asp Gly Asp Ile Ala Gln Ser Ala Asn Phe
                 80                  85                  90

Asn Arg Thr Asp Pro Ala Leu Glu Phe Gln Asn Asn Leu Ile Ser
                 95                 100                 105

Gly Phe Ser Gly Ser Ile Gly Tyr Ala Met Asp Gly Pro Arg Ile
                110                 115                 120

Glu Leu Glu Ala Ala Tyr Gln Lys Phe Asp Ala Lys Asn Pro Asp
                125                 130                 135

Asn Asn Asp Thr Asn Ser Gly Asp Tyr Tyr Lys Tyr Phe Gly Leu
                140                 145                 150

Ser Arg Glu Asp Ala Ile Ala Asp Lys Lys Tyr Val Val Leu Lys
                155                 160                 165

Asn Glu Gly Ile Thr Phe Met Ser Leu Met Val Asn Thr Cys Tyr
                170                 175                 180

Asp Ile Thr Ala Glu Gly Val Pro Phe Ile Pro Tyr Ala Cys Ala
                185                 190                 195

Gly Val Gly Ala Asp Leu Ile Asn Val Phe Lys Asp Phe Asn Leu
                200                 205                 210

Lys Phe Ser Tyr Gln Gly Lys Ile Gly Ile Ser Tyr Pro Ile Thr
                215                 220                 225

Pro Glu Val Ser Ala Phe Ile Gly Gly Tyr Tyr His Gly Val Ile
                230                 235                 240

Gly Asn Asn Phe Asn Lys Ile Pro Val Ile Thr Pro Val Val Leu
                245                 250                 255

Glu Gly Ala Pro Gln Thr Thr Ser Ala Leu Val Thr Ile Asp Thr
```

```
                    260                 265                 270

Gly Tyr Phe Gly Gly Glu Val Gly Val Arg Phe Thr Phe
                275                 280

<210> SEQ ID NO 15
<211> LENGTH: 280
<212> TYPE: PRT
<213> ORGANISM: Ehrlichia chaffeensis
<220> FEATURE:
<223> OTHER INFORMATION: P28-15 Outer Membrane Protein of
      Ehrlichia chaffeensis

<400> SEQUENCE: 15

Met Asn Cys Lys Lys Phe Phe Ile Thr Thr Ala Leu Ala Leu Pro
                  5                  10                  15

Met Ser Phe Leu Pro Gly Ile Leu Leu Ser Glu Pro Val Gln Asp
                 20                  25                  30

Asp Ser Val Ser Gly Asn Phe Tyr Ile Ser Gly Lys Tyr Met Pro
                 35                  40                  45

Ser Ala Ser His Phe Gly Val Phe Ser Ala Lys Glu Glu Lys Asn
                 50                  55                  60

Pro Thr Val Ala Leu Tyr Gly Leu Lys Gln Asp Trp Asn Gly Val
                 65                  70                  75

Ser Ala Ser Ser His Ala Asp Ala Asp Phe Asn Asn Lys Gly Tyr
                 80                  85                  90

Ser Phe Lys Tyr Glu Asn Asn Pro Phe Leu Gly Phe Ala Gly Ala
                 95                 100                 105

Ile Gly Tyr Ser Met Gly Gly Pro Arg Ile Glu Phe Glu Val Ser
                110                 115                 120

Tyr Glu Thr Phe Asp Val Lys Asn Gln Gly Gly Asn Tyr Lys Asn
                125                 130                 135

Asp Ala His Arg Tyr Cys Ala Leu Asp Arg Lys Ala Ser Ser Thr
                140                 145                 150

Asn Ala Thr Ala Ser His Tyr Val Leu Leu Lys Asn Glu Gly Leu
                155                 160                 165

Leu Asp Ile Ser Leu Met Leu Asn Ala Cys Tyr Asp Val Val Ser
                170                 175                 180

Glu Gly Ile Pro Phe Ser Pro Tyr Ile Cys Ala Gly Val Gly Thr
                185                 190                 195

Asp Leu Ile Ser Met Phe Glu Ala Ile Asn Pro Lys Ile Ser Tyr
                200                 205                 210

Gln Gly Lys Leu Gly Leu Ser Tyr Ser Ile Asn Pro Glu Ala Ser
                215                 220                 225

Val Phe Val Gly Gly His Phe His Lys Val Ala Gly Asn Glu Phe
                230                 235                 240

Arg Asp Ile Ser Thr Leu Lys Ala Phe Ala Thr Pro Ser Ser Ala
                245                 250                 255

Ala Thr Pro Asp Leu Ala Thr Val Thr Leu Ser Val Cys His Phe
                260                 265                 270

Gly Val Glu Leu Gly Gly Arg Phe Asn Phe
                275                 280

<210> SEQ ID NO 16
<211> LENGTH: 286
<212> TYPE: PRT
<213> ORGANISM: Ehrlichia chaffeensis
<220> FEATURE:
```

<223> OTHER INFORMATION: P28-16 Outer Membrane Protein of
      Ehrlichia chaffeensis

<400> SEQUENCE: 16

```
Met Asn Cys Glu Lys Phe Phe Ile Thr Thr Ala Leu Thr Leu Leu
                5                   10                  15

Met Ser Phe Leu Pro Gly Ile Ser Leu Ser Asp Pro Val Gln Asp
                20                  25                  30

Asp Asn Ile Ser Gly Asn Phe Tyr Ile Ser Gly Lys Tyr Met Pro
                35                  40                  45

Ser Ala Ser His Phe Gly Val Phe Ser Ala Lys Glu Glu Arg Asn
                50                  55                  60

Thr Thr Val Gly Val Phe Gly Ile Glu Gln Asp Trp Asp Arg Cys
                65                  70                  75

Val Ile Ser Arg Thr Thr Leu Ser Asp Ile Phe Thr Val Pro Asn
                80                  85                  90

Tyr Ser Phe Lys Tyr Glu Asn Asn Leu Phe Ser Gly Phe Ala Gly
                95                  100                 105

Ala Ile Gly Tyr Ser Met Asp Gly Pro Arg Ile Glu Leu Glu Val
                110                 115                 120

Ser Tyr Glu Ala Phe Asp Val Lys Asn Gln Gly Asn Asn Tyr Lys
                125                 130                 135

Asn Glu Ala His Arg Tyr Tyr Ala Leu Ser His Leu Leu Gly Thr
                140                 145                 150

Glu Thr Gln Ile Asp Gly Ala Gly Ser Ala Ser Val Phe Leu Ile
                155                 160                 165

Asn Glu Gly Leu Leu Asp Lys Ser Phe Met Leu Asn Ala Cys Tyr
                170                 175                 180

Asp Val Ile Ser Glu Gly Ile Pro Phe Ser Pro Tyr Ile Cys Ala
                185                 190                 195

Gly Ile Gly Ile Asp Leu Val Ser Met Phe Glu Ala Ile Asn Pro
                200                 205                 210

Lys Ile Ser Tyr Gln Gly Lys Leu Gly Leu Ser Tyr Pro Ile Ser
                215                 220                 225

Pro Glu Ala Ser Val Phe Ile Gly Gly His Phe His Lys Val Ile
                230                 235                 240

Gly Asn Glu Phe Arg Asp Ile Pro Thr Met Ile Pro Ser Glu Ser
                245                 250                 255

Ala Leu Ala Gly Lys Gly Asn Tyr Pro Ala Ile Val Thr Leu Asp
                260                 265                 270

Val Phe Tyr Phe Gly Ile Glu Leu Gly Gly Arg Phe Asn Phe Gln
                275                 280                 285

Leu
```

<210> SEQ ID NO 17
<211> LENGTH: 278
<212> TYPE: PRT
<213> ORGANISM: Ehrlichia chaffeensis
<220> FEATURE:
<223> OTHER INFORMATION: P28-17 Outer Membrane Protein of
      Ehrlichia chaffeensis

<400> SEQUENCE: 17

```
Met Asn Cys Lys Lys Phe Phe Ile Thr Thr Ala Leu Val Ser Leu
                5                   10                  15

Met Ser Phe Leu Pro Gly Ile Ser Phe Ser Asp Pro Val Gln Gly
```

```
                      20                  25                  30

Asp Asn Ile Ser Gly Asn Phe Tyr Val Ser Gly Lys Tyr Met Pro
                  35                  40                  45

Ser Ala Ser His Phe Gly Met Phe Ser Ala Lys Glu Glu Lys Asn
                  50                  55                  60

Pro Thr Val Ala Leu Tyr Gly Leu Lys Gln Asp Trp Glu Gly Ile
                  65                  70                  75

Ser Ser Ser Ser His Asn Asp Asn His Phe Asn Asn Lys Gly Tyr
                  80                  85                  90

Ser Phe Lys Tyr Glu Asn Asn Pro Phe Leu Gly Phe Ala Gly Ala
                  95                 100                 105

Ile Gly Tyr Ser Met Gly Gly Pro Arg Val Glu Phe Glu Val Ser
                 110                 115                 120

Tyr Glu Thr Phe Asp Val Lys Asn Gln Gly Asn Asn Tyr Lys Asn
                 125                 130                 135

Asp Ala His Arg Tyr Cys Ala Leu Gly Gln Gln Asp Asn Ser Gly
                 140                 145                 150

Ile Pro Lys Thr Ser Lys Tyr Val Leu Leu Lys Ser Glu Gly Leu
                 155                 160                 165

Leu Asp Ile Ser Phe Met Leu Asn Ala Cys Tyr Asp Ile Ile Asn
                 170                 175                 180

Glu Ser Ile Pro Leu Ser Pro Tyr Ile Cys Ala Gly Val Gly Thr
                 185                 190                 195

Asp Leu Ile Ser Met Phe Glu Ala Thr Asn Pro Lys Ile Ser Tyr
                 200                 205                 210

Gln Gly Lys Leu Gly Leu Ser Tyr Ser Ile Asn Pro Glu Ala Ser
                 215                 220                 225

Val Phe Ile Gly Gly His Phe His Lys Val Ile Gly Asn Glu Phe
                 230                 235                 240

Arg Asp Ile Pro Thr Leu Lys Ala Phe Val Thr Ser Ser Ala Thr
                 245                 250                 255

Pro Asp Leu Ala Ile Val Thr Leu Ser Val Cys His Phe Gly Ile
                 260                 265                 270

Glu Leu Gly Gly Arg Phe Asn Phe
                 275

<210> SEQ ID NO 18
<211> LENGTH: 280
<212> TYPE: PRT
<213> ORGANISM: Ehrlichia chaffeensis
<220> FEATURE:
<223> OTHER INFORMATION: P28-18 Outer Membrane Protein of
      Ehrlichia chaffeensis

<400> SEQUENCE: 18

Met Asn Cys Lys Lys Phe Phe Ile Thr Thr Thr Leu Val Ser Leu
                   5                  10                  15

Met Ser Phe Leu Pro Gly Ile Ser Phe Ser Asp Ala Val Gln Asn
                  20                  25                  30

Asp Asn Val Gly Gly Asn Phe Tyr Ile Ser Gly Lys Tyr Val Pro
                  35                  40                  45

Ser Val Ser His Phe Gly Val Phe Ser Ala Lys Gln Glu Arg Asn
                  50                  55                  60

Thr Thr Ile Gly Val Phe Gly Leu Lys Gln Asp Trp Asp Gly Ser
                  65                  70                  75
```

```
Thr Ile Ser Lys Asn Ser Pro Glu Asn Thr Phe Asn Val Pro Asn
                 80                  85                  90

Tyr Ser Ph

```
Glu Ala His Arg Tyr Cys Ala Leu Ser His Asn Ser Ala Ala Asp
            140                 145                 150

Met Ser Ser Ala Ser Asn Asn Phe Val Phe Leu Lys Asn Glu Gly
            155                 160                 165

Leu Leu Asp Ile Ser Phe Met Leu Asn Ala Cys Tyr Asp Val Val
            170                 175                 180

Gly Glu Gly Ile Pro Phe Ser Pro Tyr Ile Cys Ala Gly Ile Gly
            185                 190                 195

Thr Asp Leu Val Ser Met Phe Glu Ala Thr Asn Pro Lys Ile Ser
            200                 205                 210

Tyr Gln Gly Lys Leu Gly Leu Ser Tyr Ser Ile Ser Pro Glu Ala
            215                 220                 225

Ser Val Phe Ile Gly Gly His Phe His Lys Val Ile Gly Asn Glu
            230                 235                 240

Phe Arg Asp Ile Pro Thr Ile Ile Pro Thr Gly Ser Thr Leu Ala
            245                 250                 255

Gly Lys Gly Asn Tyr Pro Ala Ile Val Ile Leu Asp Val Cys His
            260                 265                 270

Phe Gly Ile Glu Leu Gly Gly Arg Phe Ala Phe
            275                 280

<210> SEQ ID NO 20
<211> LENGTH: 271
<212> TYPE: PRT
<213> ORGANISM: Ehrlichia chaffeensis
<220> FEATURE:
<223> OTHER INFORMATION: P28-20 Outer Membrane Protein of
      Ehrlichia chaffeensis

<400> SEQUENCE: 20

Met Asn Tyr Lys Lys Phe Val Val Gly Val Ala Leu Ala Thr Leu
              5                  10                  15

Leu Ser Phe Leu Pro Asp Asn Ser Phe Ser Asp Ala Asn Val Pro
             20                  25                  30

Glu Gly Arg Lys Gly Phe Tyr Val Gly Thr Gln Tyr Lys Val Gly
             35                  40                  45

Val Pro Asn Phe Ser Asn Phe Ser Ala Glu Glu Thr Leu Pro Gly
             50                  55                  60

Leu Thr Lys Ser Ile Phe Ala Leu Gly Leu Asp Lys Ser Ser Ile
             65                  70                  75

Ser Asp His Ala Gly Phe Thr Gln Ala Tyr Asn Pro Thr Tyr Ala
             80                  85                  90

Ser Asn Phe Ala Gly Phe Gly Gly Val Ile Gly Tyr Tyr Val Asn
             95                 100                 105

Asp Phe Arg Val Glu Phe Glu Gly Ala Tyr Glu Asn Phe Glu Pro
            110                 115                 120

Glu Arg Gln Trp Tyr Pro Glu Gly Gly Glu Ser His Lys Phe Phe
            125                 130                 135

Ala Leu Ser Arg Glu Ser Thr Val Gln Asp Asn Lys Phe Ile Val
            140                 145                 150

Leu Glu Asn Asp Gly Val Ile Asp Lys Ser Leu Asn Val Asn Phe
            155                 160                 165

Cys Tyr Asp Ile Ala His Gly Ser Ile Pro Leu Ala Pro Tyr Met
            170                 175                 180

Cys Ala Gly Val Gly Ala Asp Tyr Ile Lys Phe Leu Gly Ile Ser
```

```
                    185                 190                 195
Leu Pro Lys Phe Ser Tyr Gln Val Lys Phe Gly Val Asn Tyr Pro
                200                 205                 210

Val Ser Val Asn Val Met Leu Phe Gly Gly Tyr Tyr His Lys
                215                 220                 225

Val Ile Gly Asn Arg Tyr Glu Arg Val Glu Ile Ala Tyr His Pro
                230                 235                 240

Ala Thr Leu Thr Asn Val Pro Lys Thr Thr Ser Ala Ser Ala Thr
                245                 250                 255

Leu Asp Thr Asp Tyr Phe Gly Trp Glu Val Gly Met Arg Phe Thr
                260                 265                 270

Leu

<210> SEQ ID NO 21
<211> LENGTH: 279
<212> TYPE: PRT
<213> ORGANISM: Ehrlichia chaffeensis
<220> FEATURE:
<223> OTHER INFORMATION: P28-21 Outer Membrane Protein of
      Ehrlichia chaffeensis

<400> SEQUENCE: 21

Met Arg Tyr Lys Asp Phe Ser Asn Asn Ile Asp Val Ile Ile Gly
                  5                  10                  15

Thr Leu Val Gly Cys Phe Ser Gly Ser Leu Asp Val Ser Asp Ser
                 20                  25                  30

Leu Asn Ser Arg Leu Lys Pro Val Phe Leu Gly Ile Ser Tyr Lys
                 35                  40                  45

Leu Ser Ala Pro Leu Phe Ser Ser Phe Ser Ile Gly Glu Thr Tyr
                 50                  55                  60

Arg Ile Asn Gly Val Lys Thr Asp Arg Val Val Gly Leu Lys Ser
                 65                  70                  75

Asp Ile Leu Leu Asp Ala Asp Lys Ala Met Lys Asp Phe Asn Asn
                 80                  85                  90

Phe Asn Phe Ser Glu Glu Tyr Val Pro Lys Tyr Asp Asn Asn Ile
                 95                 100                 105

Phe Gly Leu Ser Phe Ile Phe Gly Tyr Ser Phe Arg Asn Leu Arg
                110                 115                 120

Val Glu Leu Glu Gly Ser Tyr Lys Lys Phe Asp Val Ile Asp Thr
                125                 130                 135

Arg Asn His Leu Val Asp Asn Asn Tyr Arg His Ile Ala Leu Val
                140                 145                 150

Arg Ser Asn Pro Pro Thr Leu Tyr Asp Tyr Phe Val Leu Lys Asn
                155                 160                 165

Asp Gly Val Glu Phe Tyr Ser Thr Ile Leu Asn Ile Cys Tyr Asp
                170                 175                 180

Phe Ala Val Asp Thr Asn Ile Val Pro Phe Ser Cys Val Gly Ile
                185                 190                 195

Gly Glu Asp Ile Ile Lys Ile Phe Asp Ser Ile Arg Phe Lys Pro
                200                 205                 210

Ser Phe Asn Ser Lys Leu Gly Ile Asn Tyr Leu Met Ser Gln Asp
                215                 220                 225

Met Leu Leu Phe Phe Asp Val Tyr Tyr His Arg Val Val Gly Asn
                230                 235                 240

Glu Tyr Asn Asn Ile Pro Val Gln Tyr Val Ser Leu Pro Asn Pro
```

-continued

```
                    245                 250                 255
Leu Asn Ile Ser Thr Ala Ala Lys Leu Asp Met Glu Tyr Phe Gly
            260                 265                 270

Ala Glu Ile Gly Ile Lys Val Phe Val
            275

<210> SEQ ID NO 22
<211> LENGTH: 23
<212> TYPE: DNA
<213> ORGANISM: artificial sequence
<220> FEATURE:
<221> NAME/KEY: primer_bind
<223> OTHER INFORMATION: P28-10 forward primer

<400> SEQUENCE: 22
acgtgatatg gaaagcaaca agt                                        23

<210> SEQ ID NO 23
<211> LENGTH: 18
<212> TYPE: DNA
<213> ORGANISM: artificial sequence
<220> FEATURE:
<221> NAME/KEY: primer_bind
<223> OTHER INFORMATION: P28-10 reverse primer

<400> SEQUENCE: 23
gcgccgaaat atccaaca                                              18

<210> SEQ ID NO 24
<211> LENGTH: 22
<212> TYPE: DNA
<213> ORGANISM: artificial sequence
<220> FEATURE:
<221> NAME/KEY: primer_bind
<223> OTHER INFORMATION: P28-11 forward primer

<400> SEQUENCE: 24
ggtcaaactt gccctaaaca ca                                         22

<210> SEQ ID NO 25
<211> LENGTH: 24
<212> TYPE: DNA
<213> ORGANISM: artificial sequence
<220> FEATURE:
<221> NAME/KEY: primer_bind
<223> OTHER INFORMATION: P28-11 reverse primer

<400> SEQUENCE: 25
acttcaccac caaaataccc aata                                       24

<210> SEQ ID NO 26
<211> LENGTH: 19
<212> TYPE: DNA
<213> ORGANISM: artificial sequence
<220> FEATURE:
<221> NAME/KEY: primer_bind
<223> OTHER INFORMATION: P28-12 forward primer

<400> SEQUENCE: 26
ctgctggcat tagttaccc                                             19

<210> SEQ ID NO 27
<211> LENGTH: 17
<212> TYPE: DNA
<213> ORGANISM: artificial sequence
<220> FEATURE:
```

```
<221> NAME/KEY: primer_bind
<223> OTHER INFORMATION: P28-12 reverse primer

<400> SEQUENCE: 27
catagcagcc attgacc                                                17

<210> SEQ ID NO 28
<211> LENGTH: 24
<212> TYPE: DNA
<213> ORGANISM: artificial sequence
<220> FEATURE:
<221> NAME/KEY: primer_bind
<223> OTHER INFORMATION: P28-13 forward primer

<400> SEQUENCE: 28
attgattgcc tattacttga tggt                                        24

<210> SEQ ID NO 29
<211> LENGTH: 20
<212> TYPE: DNA
<213> ORGANISM: artificial sequence
<220> FEATURE:
<221> NAME/KEY: primer_bind
<223> OTHER INFORMATION: P28-13 reverse primer

<400> SEQUENCE: 29
aatggggctg ttggttactc                                             20

<210> SEQ ID NO 30
<211> LENGTH: 23
<212> TYPE: DNA
<213> ORGANISM: artificial sequence
<220> FEATURE:
<221> NAME/KEY: primer_bind
<223> OTHER INFORMATION: P28-14 forward primer

<400> SEQUENCE: 30
tgaagacgca atagcagata aga                                         23

<210> SEQ ID NO 31
<211> LENGTH: 20
<212> TYPE: DNA
<213> ORGANISM: artificial sequence
<220> FEATURE:
<221> NAME/KEY: primer_bind
<223> OTHER INFORMATION: P28-14 reverse primer

<400> SEQUENCE: 31
tagcgcagat gtggtttgag                                             20

<210> SEQ ID NO 32
<211> LENGTH: 21
<212> TYPE: DNA
<213> ORGANISM: artificial sequence
<220> FEATURE:
<221> NAME/KEY: primer_bind
<223> OTHER INFORMATION: P28-15 forward primer

<400> SEQUENCE: 32
actgtcgcgt tgtatggttt g                                           21

<210> SEQ ID NO 33
<211> LENGTH: 22
<212> TYPE: DNA
<213> ORGANISM: artificial sequence
<220> FEATURE:
<221> NAME/KEY: primer_bind
```

<223> OTHER INFORMATION: P28-15 reverse primer

<400> SEQUENCE: 33
attagtgctg cttgctttac ga					22

<210> SEQ ID NO 34
<211> LENGTH: 24
<212> TYPE: DNA
<213> ORGANISM: artificial sequence
<220> FEATURE:
<221> NAME/KEY: primer_bind
<223> OTHER INFORMATION: P28-17 forward primer

<400> SEQUENCE: 34
tgcaaggtga caatattagt ggta					24

<210> SEQ ID NO 35
<211> LENGTH: 22
<212> TYPE: DNA
<213> ORGANISM: artificial sequence
<220> FEATURE:
<221> NAME/KEY: primer_bind
<223> OTHER INFORMATION: P28-17 reverse primer

<400> SEQUENCE: 35
gtattccgct gttgtcttgt tg					22

<210> SEQ ID NO 36
<211> LENGTH: 21
<212> TYPE: DNA
<213> ORGANISM: artificial sequence
<220> FEATURE:
<221> NAME/KEY: primer_bind
<223> OTHER INFORMATION: P28-18 forward primer

<400> SEQUENCE: 36
acattttggc gtattctctg c					21

<210> SEQ ID NO 37
<211> LENGTH: 21
<212> TYPE: DNA
<213> ORGANISM: artificial sequence
<220> FEATURE:
<221> NAME/KEY: primer_bind
<223> OTHER INFORMATION: P28-18 reverse primer

<400> SEQUENCE: 37
tagctttccc ccactgttat g					21

<210> SEQ ID NO 38
<211> LENGTH: 24
<212> TYPE: DNA
<213> ORGANISM: artificial sequence
<220> FEATURE:
<221> NAME/KEY: primer_bind
<223> OTHER INFORMATION: P28-20 forward primer

<400> SEQUENCE: 38
aacttatggc tttctcctcc tttc					24

<210> SEQ ID NO 39
<211> LENGTH: 24
<212> TYPE: DNA
<213> ORGANISM: artificial sequence
<220> FEATURE:
<221> NAME/KEY: primer_bind
<223> OTHER INFORMATION: P28-20 reverse primer

```
<400> SEQUENCE: 39
ttgcctgata attcttttc tgat                                          24

<210> SEQ ID NO 40
<211> LENGTH: 24
<212> TYPE: DNA
<213> ORGANISM: artificial sequence
<220> FEATURE:
<221> NAME/KEY: primer_bind
<223> OTHER INFORMATION: P28-21 forward primer

<400> SEQUENCE: 40
accaacttcc caaccaaaat aatc                                         24

<210> SEQ ID NO 41
<211> LENGTH: 24
<212> TYPE: DNA
<213> ORGANISM: artificial sequence
<220> FEATURE:
<221> NAME/KEY: primer_bind
<223> OTHER INFORMATION: P28-21 reverse primer

<400> SEQUENCE: 41
ctgaaggagg agaaagccat aagt                                         24

<210> SEQ ID NO 42
<211> LENGTH: 23
<212> TYPE: DNA
<213> ORGANISM: artificial sequence
<220> FEATURE:
<221> NAME/KEY: primer_bind
<223> OTHER INFORMATION: 1a-r1 primer

<400> SEQUENCE: 42
accaaagtat gcaatgtcaa gtg                                          23

<210> SEQ ID NO 43
<211> LENGTH: 25
<212> TYPE: DNA
<213> ORGANISM: artificial sequence
<220> FEATURE:
<221> NAME/KEY: primer_bind
<223> OTHER INFORMATION: 1a-r2 primer

<400> SEQUENCE: 43
ctgcagatgt gactttagga gattc                                        25

<210> SEQ ID NO 44
<211> LENGTH: 23
<212> TYPE: DNA
<213> ORGANISM: artificial sequence
<220> FEATURE:
<221> NAME/KEY: primer_bind
<223> OTHER INFORMATION: 28r3 primer

<400> SEQUENCE: 44
tgtatatctt ccagggtctt tga                                          23

<210> SEQ ID NO 45
<211> LENGTH: 18
<212> TYPE: DNA
<213> ORGANISM: artificial sequence
<220> FEATURE:
<221> NAME/KEY: primer_bind
<223> OTHER INFORMATION: pvur32 primer
```

```
<400> SEQUENCE: 45
gaccattcta cctcaacc                                                    18

<210> SEQ ID NO 46
<211> LENGTH: 22
<212> TYPE: DNA
<213> ORGANISM: artificial sequence
<220> FEATURE:
<221> NAME/KEY: primer_bind
<223> OTHER INFORMATION: 28r10 primer

<400> SEQUENCE: 46
atatccaatt gctccactga aa                                               22

<210> SEQ ID NO 47
<211> LENGTH: 30
<212> TYPE: DNA
<213> ORGANISM: artificial sequence
<220> FEATURE:
<221> NAME/KEY: primer_bind
<223> OTHER INFORMATION: 28r12 primer

<400> SEQUENCE: 47
cttgaaatgt aacagtatat ggaccttgaa                                       30

<210> SEQ ID NO 48
<211> LENGTH: 20
<212> TYPE: DNA
<213> ORGANISM: artificial sequence
<220> FEATURE:
<221> NAME/KEY: primer_bind
<223> OTHER INFORMATION: 28stur primer

<400> SEQUENCE: 48
tgtccttttt aagcccaact                                                  20

<210> SEQ ID NO 49
<211> LENGTH: 24
<212> TYPE: DNA
<213> ORGANISM: artificial sequence
<220> FEATURE:
<221> NAME/KEY: primer_bind
<223> OTHER INFORMATION: 28r14 primer

<400> SEQUENCE: 49
ttctgcagat tgatgtggat gttt                                             24

<210> SEQ ID NO 50
<211> LENGTH: 21
<212> TYPE: DNA
<213> ORGANISM: artificial sequence
<220> FEATURE:
<221> NAME/KEY: primer_bind
<223> OTHER INFORMATION: 28r15 primer

<400> SEQUENCE: 50
tgcagattga tgtggatgtt t                                                21

<210> SEQ ID NO 51
<211> LENGTH: 22
<212> TYPE: DNA
<213> ORGANISM: artificial sequence
<220> FEATURE:
<221> NAME/KEY: primer_bind
<223> OTHER INFORMATION: 28f1 primer

<400> SEQUENCE: 51
```

```
gtaaaacaca agccaccagt ct                                              22

<210> SEQ ID NO 52
<211> LENGTH: 24
<212> TYPE: DNA
<213> ORGANISM: artificial sequence
<220> FEATURE:
<221> NAME/KEY: primer_bind
<223> OTHER INFORMATION: 28f2 primer

<400> SEQUENCE: 52
gggcatatac ctacaccaaa cacc                                            24

<210> SEQ ID NO 53
<211> LENGTH: 21
<212> TYPE: DNA
<213> ORGANISM: artificial sequence
<220> FEATURE:
<221> NAME/KEY: primer_bind
<223> OTHER INFORMATION: 28f3 primer

<400> SEQUENCE: 53
taagaggatt gggtaaggat a                                               21
```